(12) United States Patent
Dinville

(10) Patent No.: US 10,350,088 B2
(45) Date of Patent: *Jul. 16, 2019

(54) INSTRUMENTATION AND METHODS FOR INSERTING AN INTERVERTEBRAL DISC PROSTHESIS

(71) Applicant: LDR Medical, Rosières Près Troyes (FR)

(72) Inventor: Hervé Dinville, St Parres aux Tertres (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/012,815

(22) Filed: Feb. 1, 2016

(65) Prior Publication Data

US 2016/0220389 A1    Aug. 4, 2016

Related U.S. Application Data

(63) Continuation of application No. 13/892,933, filed on May 13, 2013, now Pat. No. 9,248,025, which is a
(Continued)

(30) Foreign Application Priority Data

Jun. 29, 2005    (FR) ..................... 05 06652

(51) Int. Cl.
*A61B 17/88* (2006.01)
*A61F 2/46* (2006.01)
(Continued)

(52) U.S. Cl.
CPC ........ *A61F 2/4611* (2013.01); *A61B 17/1671* (2013.01); *A61B 17/1757* (2013.01);
(Continued)

(58) Field of Classification Search
CPC ................. A61F 2/4611; A61F 2/442; A61F 2002/30538; A61F 2002/30884;
(Continued)

(56) References Cited

U.S. PATENT DOCUMENTS 1,436,573 A    11/1922    Choppinet et al.
2,836,442 A    5/1958     Moskovitz
(Continued)

FOREIGN PATENT DOCUMENTS

DE    2263842 A1    7/1974
DE    2804936 A1    8/1979
(Continued)

OTHER PUBLICATIONS

"Applicants' Response filed Aug. 18, 2009 to USPTO OA of Feb. 18, 2009 in U.S. Appl. No. 11/632,253", 15 pgs.
(Continued)

*Primary Examiner* — Pedro Philogene
*Assistant Examiner* — David C Comstock
(74) *Attorney, Agent, or Firm* — Schwegman Lundberg & Woessner, P.A.

(57) ABSTRACT

Embodiments of instrumentation and methods are provided for the insertion of intervertebral disc prosthesis. The instrumentation of the embodiments comprises a guide comprising at least two lateral faces, at least one upper plate, at least one lower plate, at least one retainer, a cage defining an insertion axis for the prosthesis, and an angle adjuster adapted to adjust an angle formed by the insertion axis and an antero-posterior sagittal axis; and at least one separator sized to maintain a gap between the upper vertebra and the lower vertebra. Methods for implanting a prosthesis using the disclosed instrumentation comprise implanting a pin in the median sagittal axis of a vertebrae; measuring the dimensions of the intervertebral space; choosing the pros-
(Continued)

thesis; choosing the guide; adjusting the angle adjuster; positioning the guide adjacent to the intervertebral space; inserting the prosthesis into the guide; and inserting the prosthesis into the intervertebral space.

20 Claims, 11 Drawing Sheets

Related U.S. Application Data continuation of application No. 12/435,955, filed on May 5, 2009, now Pat. No. 8,439,931, which is a continuation of application No. 11/180,868, filed on Jul. 13, 2005, now Pat. No. 7,632,282.

(51) Int. Cl.
  *A61F 2/44* (2006.01)
  *A61B 17/16* (2006.01)
  *A61B 17/17* (2006.01)
  *A61F 2/30* (2006.01)

(52) U.S. Cl.
  CPC .......... *A61F 2/442* (2013.01); *A61B 17/1604* (2013.01); *A61B 17/1735* (2013.01); *A61F 2002/30538* (2013.01); *A61F 2002/30884* (2013.01); *A61F 2002/4627* (2013.01); *A61F 2002/4658* (2013.01); *A61F 2002/4668* (2013.01); *A61F 2002/4687* (2013.01); *A61F 2250/0006* (2013.01)

(58) Field of Classification Search
  CPC ...... A61F 2002/4627; A61F 2002/4658; A61F 2002/4668; A61F 2002/4687; A61F 2250/0006; A61B 17/1671; A61B 17/1757; A61B 17/1604; A61B 17/1735
  USPC ....... 606/246, 279, 79, 84, 86 R, 87, 90, 96, 606/99, 102, 104, 105, 86 A; 623/17.11–17.16
  See application file for complete search history.

(56) References Cited

U.S. PATENT DOCUMENTS

| | | |
|---|---|---|
| 3,325,197 A | 6/1967 | Wehner |
| 3,486,505 A | 12/1969 | Morrison |
| 3,857,642 A | 12/1974 | Miller |
| 3,958,278 A | 5/1976 | Lee et al. |
| 4,074,542 A | 2/1978 | Hankosky et al. |
| 4,085,466 A | 4/1978 | Goodfellow et al. |
| 4,309,777 A | 1/1982 | Patil |
| 4,349,921 A | 9/1982 | Kuntz |
| 4,655,778 A | 4/1987 | Koeneman |
| 4,714,469 A | 12/1987 | Kenna |
| 4,756,711 A | 7/1988 | Mai et al. |
| 4,759,766 A | 7/1988 | Buettner-Janz et al. |
| 4,759,769 A | 7/1988 | Hedman et al. |
| 4,787,908 A | 11/1988 | Wyss et al. |
| 4,863,476 A | 9/1989 | Shepperd |
| 4,874,389 A | 10/1989 | Downey |
| 4,892,545 A | 1/1990 | Day et al. |
| 4,911,718 A | 3/1990 | Lee et al. |
| 4,932,975 A | 6/1990 | Main et al. |
| 4,946,378 A | 8/1990 | Hirayama et al. |
| 4,955,908 A | 9/1990 | Frey et al. |
| 4,955,916 A | 9/1990 | Carignan et al. |
| 4,997,432 A | 3/1991 | Keller |
| 5,002,576 A | 3/1991 | Fuhrmann et al. |
| 5,041,139 A | 8/1991 | Branemark |
| 5,071,437 A | 12/1991 | Steffee Arthur D |
| 5,122,130 A | 6/1992 | Keller |
| 5,123,926 A | 6/1992 | Pisharodi |
| 5,171,281 A | 12/1992 | Parsons et al. |
| 5,192,327 A | 3/1993 | Brantigan |
| 5,197,986 A | 3/1993 | Mikhail |
| 5,246,458 A | 9/1993 | Graham |
| 5,258,031 A | 11/1993 | Salib et al. |
| 5,290,312 A | 3/1994 | Kojimoto |
| 5,306,309 A | 4/1994 | Wagner et al. |
| 5,314,477 A | 5/1994 | Marnay |
| 5,358,526 A | 10/1994 | Tornier |
| 5,370,697 A | 12/1994 | Baumgartner |
| 5,397,364 A | 3/1995 | Kozak et al. |
| 5,401,269 A | 3/1995 | Buttner-Janz et al. |
| 5,425,773 A | 6/1995 | Boyd et al. |
| 5,507,816 A | 4/1996 | Bullivant |
| 5,534,029 A | 7/1996 | Shima |
| 5,534,030 A | 7/1996 | Navarro et al. |
| 566,360 A | 8/1996 | White |
| 5,545,229 A | 8/1996 | Parsons et al. |
| 5,556,431 A | 9/1996 | Buttner-Janz |
| 5,562,738 A | 10/1996 | Boyd et al. |
| 5,571,109 A | 11/1996 | Bertagnoli |
| 5,609,636 A | 3/1997 | Kohrs et al. |
| 5,645,596 A | 7/1997 | Kim et al. |
| 5,674,294 A | 10/1997 | Bainville et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,824,094 A | 10/1998 | Serhan et al. |
| 5,827,328 A | 12/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,088 A | 5/2000 | Winslow |
| 6,063,121 A | 5/2000 | Xavier et al. |
| 6,080,158 A | 6/2000 | Lin |
| 6,093,205 A | 7/2000 | McLeod et al. |
| 6,096,038 A | 8/2000 | Michelson |
| 6,096,080 A | 8/2000 | Nicholson et al. |
| 6,113,637 A | 9/2000 | Gill et al. |
| 6,113,638 A | 9/2000 | Williams et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |

(56) References Cited

U.S. PATENT DOCUMENTS

| | | |
|---|---|---|
| 6,270,498 B1 | 8/2001 | Michelson et al. |
| 6,277,149 B1 | 8/2001 | Boyle et al. |
| 6,283,998 B1 | 9/2001 | Eaton |
| 6,296,664 B1 | 10/2001 | Middleton |
| 6,306,170 B2 | 10/2001 | Ray |
| 6,315,797 B1 | 11/2001 | Middleton |
| 6,319,257 B1 | 11/2001 | Carignan et al. |
| 6,344,057 B1 | 2/2002 | Rabbe et al. |
| 6,364,880 B1 | 4/2002 | Michelson |
| 6,368,350 B1 | 4/2002 | Erickson et al. |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,704 B1 | 7/2002 | Ferree |
| 6,419,706 B1 | 7/2002 | Graf |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,546 B1 | 9/2002 | Bramlet et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,572,653 B1 | 6/2003 | Simonson |
| 6,579,291 B1 | 6/2003 | Keith et al. |
| 6,579,320 B1 | 6/2003 | Gauchet et al. |
| 6,582,468 B1 | 6/2003 | Gauchet |
| 6,592,624 B1 | 7/2003 | Fraser et al. |
| 6,599,294 B2 | 7/2003 | Fuss et al. |
| 6,599,320 B1 | 7/2003 | Kuslich |
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,616,671 B2 | 9/2003 | Landry et al. |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,719,794 B2 | 4/2004 | Gerber et al. |
| 6,723,127 B2 | 4/2004 | Ralph et al. |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,793,678 B2 | 9/2004 | Hawkins |
| 6,800,093 B2 | 10/2004 | Nicholson et al. |
| 6,814,737 B2 | 11/2004 | Cauthen |
| 6,824,565 B2 | 11/2004 | Muhanna et al. |
| 6,899,735 B2 | 5/2005 | Coates et al. |
| 6,936,071 B1 | 8/2005 | Marnay et al. |
| 6,964,686 B2 | 11/2005 | Gordon |
| 6,966,929 B2 | 11/2005 | Mitchell |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,432 B2 | 2/2006 | Keller et al. |
| 7,011,684 B2 | 3/2006 | Eckman |
| 7,025,787 B2 | 4/2006 | Bryan et al. |
| 7,037,340 B2 | 5/2006 | Gau |
| 7,056,344 B2 | 6/2006 | Huppert et al. |
| 7,060,097 B2 | 6/2006 | Fraser et al. |
| 7,060,099 B2 | 6/2006 | Carli et al. |
| 7,105,023 B2 | 9/2006 | Eckman |
| 7,105,024 B2 | 9/2006 | Richelsoph |
| 7,118,580 B1 | 10/2006 | Beyersdorff et al. |
| 7,153,325 B2 | 12/2006 | Kim et al. |
| 7,169,153 B2 | 1/2007 | Keller |
| 7,175,662 B2 | 2/2007 | Link et al. |
| 7,198,644 B2 | 4/2007 | Schultz et al. |
| 7,204,851 B2 | 4/2007 | Trieu et al. |
| 7,204,852 B2 | 4/2007 | Marnay et al. |
| 7,291,170 B2 | 11/2007 | Huppert |
| 7,326,250 B2 | 2/2008 | Beaurain et al. |
| 7,419,505 B2 | 9/2008 | Fleischmann et al. |
| 7,494,508 B2 | 2/2009 | Zeegers |
| 7,507,248 B2 | 3/2009 | Beaurain et al. |
| 7,594,931 B2 | 9/2009 | Louis et al. |
| 7,632,282 B2 * | 12/2009 | Dinville .............. A61B 17/1671 606/99 |
| 7,682,396 B2 | 3/2010 | Beaurain et al. |
| 7,695,516 B2 | 4/2010 | Zeegers |
| 7,695,518 B2 | 4/2010 | Gau |
| 7,842,088 B2 | 11/2010 | Rashbaum et al. |
| 8,002,835 B2 | 8/2011 | Zeegers |
| 8,147,556 B2 | 4/2012 | Louis et al. |
| 8,162,988 B2 | 4/2012 | Delecrin et al. |
| 8,221,422 B2 | 7/2012 | Mangione |
| 8,221,457 B2 | 7/2012 | Delecrin et al. |
| 8,241,359 B2 | 8/2012 | Davis et al. |
| 8,257,439 B2 | 9/2012 | Zeegers |
| 8,262,700 B2 | 9/2012 | Cho et al. |
| 8,267,999 B2 | 9/2012 | Beaurain et al. |
| 8,343,219 B2 | 1/2013 | Allain et al. |
| 8,409,288 B2 | 4/2013 | Davis et al. |
| 8,430,915 B2 | 4/2013 | Beaurain et al. |
| 8,439,931 B2 * | 5/2013 | Dinville .............. A61B 17/1671 606/246 |
| 8,465,546 B2 | 6/2013 | Jodaitis et al. |
| 8,617,245 B2 | 12/2013 | Brett |
| 8,623,087 B2 | 1/2014 | Huppert |
| 8,632,591 B2 | 1/2014 | Vila et al. |
| 8,685,100 B2 | 4/2014 | Jodaitis et al. |
| 8,753,397 B2 | 6/2014 | Beaurain et al. |
| 8,771,284 B2 | 7/2014 | Rashbaum et al. |
| 8,845,691 B2 | 9/2014 | Renaud et al. |
| 8,858,635 B2 | 10/2014 | Hovorka et al. |
| 8,920,474 B2 | 12/2014 | Delecrin et al. |
| 8,932,359 B2 | 1/2015 | Brett |
| 8,974,497 B2 | 3/2015 | Cho et al. |
| 8,974,532 B2 | 3/2015 | Zeegers |
| 8,979,932 B2 | 3/2015 | Rashbaum et al. |

(56) References Cited

U.S. PATENT DOCUMENTS

| | | | |
|---|---|---|---|
| 9,039,774 B2 | 5/2015 | Chataigner et al. | |
| 9,044,337 B2 | 6/2015 | Dinville et al. | |
| 9,044,339 B2 | 6/2015 | Zeegers | |
| 9,078,765 B2 | 7/2015 | Louis et al. | |
| 9,144,505 B2 | 9/2015 | Steib | |
| 9,248,025 B2 * | 2/2016 | Dinville | A61B 17/1671 |
| 9,265,618 B2 | 2/2016 | Rashbaum et al. | |
| 9,265,619 B2 | 2/2016 | Beaurain et al. | |
| 9,314,232 B2 * | 4/2016 | Stark | A61B 17/1757 |
| 9,333,095 B2 | 5/2016 | Beaurain et al. | |
| 9,402,658 B2 | 8/2016 | Dinville et al. | |
| 9,445,915 B2 | 9/2016 | Zeegers | |
| 9,463,091 B2 | 10/2016 | Brett | |
| 9,480,572 B2 | 11/2016 | Jodaitis et al. | |
| 9,526,622 B2 | 12/2016 | Vila et al. | |
| 9,532,882 B2 | 1/2017 | Huppert | |
| 9,549,766 B2 | 1/2017 | Delecrin et al. | |
| 9,597,194 B2 | 3/2017 | Rashbaum et al. | |
| 9,597,198 B2 | 3/2017 | Davis et al. | |
| 9,655,739 B2 | 5/2017 | Hovorka et al. | |
| 9,713,535 B2 | 7/2017 | Davis et al. | |
| 9,730,733 B2 | 8/2017 | Cho et al. | |
| 9,763,699 B2 | 9/2017 | Beaurain et al. | |
| 9,795,485 B2 | 10/2017 | Allain et al. | |
| 9,833,331 B2 | 12/2017 | Dinville et al. | |
| 9,877,842 B2 | 1/2018 | Chataigner et al. | |
| 9,974,661 B2 | 5/2018 | Dinville et al. | |
| 2001/0020185 A1 | 9/2001 | Ray | |
| 2002/0087212 A1 | 7/2002 | James et al. | |
| 2002/0143343 A1 | 10/2002 | Castro | |
| 2003/0028249 A1 | 2/2003 | Baccelli et al. | |
| 2003/0055503 A1 | 3/2003 | O'Neil et al. | |
| 2003/0069586 A1 | 4/2003 | Errico et al. | |
| 2003/0109928 A1 | 6/2003 | Pasquet et al. | |
| 2003/0149438 A1 | 8/2003 | Nichols et al. | |
| 2003/0171814 A1 | 9/2003 | Muhanna et al. | |
| 2003/0187506 A1 | 10/2003 | Ross et al. | |
| 2003/0195626 A1 | 10/2003 | Huppert | |
| 2003/0220691 A1 | 11/2003 | Songer et al. | |
| 2004/0002758 A1 | 1/2004 | Landry et al. | |
| 2004/0002761 A1 | 1/2004 | Rogers et al. | |
| 2004/0010316 A1 | 1/2004 | William et al. | |
| 2004/0030387 A1 | 2/2004 | Landry et al. | |
| 2004/0034423 A1 | 2/2004 | Lyons et al. | |
| 2004/0073309 A1 | 4/2004 | Bianchi et al. | |
| 2004/0073311 A1 | 4/2004 | Ferree | |
| 2004/0083000 A1 | 4/2004 | Keller et al. | |
| 2004/0093082 A1 | 5/2004 | Ferree | |
| 2004/0093083 A1 | 5/2004 | Branch et al. | |
| 2004/0102846 A1 | 5/2004 | Keller et al. | |
| 2004/0111160 A1 | 6/2004 | Evans et al. | |
| 2004/0117022 A1 | 6/2004 | Marnay et al. | |
| 2004/0133278 A1 | 7/2004 | Marino et al. | |
| 2004/0133281 A1 | 7/2004 | Khandkar et al. | |
| 2004/0143332 A1 | 7/2004 | Krueger et al. | |
| 2004/0148029 A1 | 7/2004 | Bianchi et al. | |
| 2004/0162617 A1 | 8/2004 | Zucherman et al. | |
| 2004/0172020 A1 | 9/2004 | Beaurain et al. | |
| 2004/0193273 A1 | 9/2004 | Huang | |
| 2004/0199254 A1 | 10/2004 | Louis et al. | |
| 2004/0220582 A1 | 11/2004 | Keller | |
| 2004/0225295 A1 | 11/2004 | Zubok et al. | |
| 2004/0225363 A1 | 11/2004 | Richelsoph | |
| 2004/0225364 A1 | 11/2004 | Richelsoph et al. | |
| 2004/0243238 A1 | 12/2004 | Arnin et al. | |
| 2004/0243240 A1 | 12/2004 | Beaurain et al. | |
| 2004/0254577 A1 | 12/2004 | Delecrin et al. | |
| 2005/0010215 A1 | 1/2005 | Delecrin et al. | |
| 2005/0015094 A1 | 1/2005 | Keller | |
| 2005/0021042 A1 | 1/2005 | Marnay et al. | |
| 2005/0027359 A1 | 2/2005 | Mashburn | |
| 2005/0027363 A1 | 2/2005 | Gordon | |
| 2005/0033305 A1 | 2/2005 | Schultz | |
| 2005/0033437 A1 | 2/2005 | Bao et al. | |
| 2005/0033438 A1 | 2/2005 | Schultz et al. | |
| 2005/0043798 A1 | 2/2005 | Eckman | |
| 2005/0043800 A1 | 2/2005 | Paul et al. | |
| 2005/0043804 A1 | 2/2005 | Gordon et al. | |
| 2005/0060034 A1 | 3/2005 | Berry et al. | |
| 2005/0065611 A1 | 3/2005 | Huppert et al. | |
| 2005/0071009 A1 | 3/2005 | Muhanna et al. | |
| 2005/0085911 A1 | 4/2005 | Link | |
| 2005/0085917 A1 | 4/2005 | Marnay et al. | |
| 2005/0107788 A1 | 5/2005 | Beaurain et al. | |
| 2005/0113842 A1 | 5/2005 | Bertagnoli et al. | |
| 2005/0113926 A1 | 5/2005 | Zucherman et al. | |
| 2005/0119665 A1 | 6/2005 | Keller | |
| 2005/0131542 A1 | 6/2005 | Benzel et al. | |
| 2005/0143824 A1 | 6/2005 | Richelsoph et al. | |
| 2005/0149189 A1 | 7/2005 | Mokhtar et al. | |
| 2005/0159818 A1 | 7/2005 | Blain | |
| 2005/0165408 A1 | 7/2005 | Puno et al. | |
| 2005/0165485 A1 | 7/2005 | Trieu | |
| 2005/0171610 A1 | 8/2005 | Humphreys et al. | |
| 2005/0192671 A1 | 9/2005 | Bao et al. | |
| 2005/0197705 A1 | 9/2005 | Arnin et al. | |
| 2005/0197706 A1 | 9/2005 | Hovorka et al. | |
| 2005/0216086 A1 | 9/2005 | Marik et al. | |
| 2005/0216092 A1 | 9/2005 | Marik et al. | |
| 2005/0228500 A1 | 10/2005 | Kim et al. | |
| 2005/0234553 A1 | 10/2005 | Gordon | |
| 2005/0240273 A1 | 10/2005 | Khandkar et al. | |
| 2005/0246024 A1 | 11/2005 | Zeegers | |
| 2005/0251260 A1 | 11/2005 | Gerber et al. | |
| 2005/0256579 A1 | 11/2005 | Keller et al. | |
| 2005/0267581 A1 | 12/2005 | Marnay et al. | |
| 2005/0283242 A1 | 12/2005 | Zucherman et al. | |
| 2006/0015183 A1 | 1/2006 | Gilbert et al. | |
| 2006/0020341 A1 | 1/2006 | Schneid et al. | |
| 2006/0030860 A1 | 2/2006 | Peterman | |
| 2006/0036326 A1 | 2/2006 | Baumgartner et al. | |
| 2006/0041313 A1 | 2/2006 | Allard et al. | |
| 2006/0041314 A1 | 2/2006 | Millard | |
| 2006/0069437 A1 | 3/2006 | Weber | |
| 2006/0069441 A1 | 3/2006 | Zucherman et al. | |
| 2006/0111783 A1 | 5/2006 | Aflatoon et al. | |
| 2006/0116768 A1 | 6/2006 | Krueger et al. | |
| 2006/0116769 A1 | 6/2006 | Marnay et al. | |
| 2006/0122703 A1 | 6/2006 | Aebi et al. | |
| 2006/0136063 A1 | 6/2006 | Zeegers | |
| 2006/0142863 A1 | 6/2006 | Fraser et al. | |
| 2006/0149273 A1 | 7/2006 | Ross et al. | |
| 2006/0149371 A1 | 7/2006 | Marik et al. | |
| 2006/0149378 A1 | 7/2006 | Chase et al. | |
| 2006/0155377 A1 | 7/2006 | Beaurain et al. | |
| 2006/0155378 A1 | 7/2006 | Eckman | |
| 2006/0173544 A1 | 8/2006 | Gau | |
| 2006/0178746 A1 | 8/2006 | Bartish et al. | |
| 2006/0190082 A1 | 8/2006 | Keller et al. | |
| 2006/0200241 A1 | 9/2006 | Rothman et al. | |
| 2006/0200242 A1 | 9/2006 | Rothman et al. | |
| 2006/0200243 A1 | 9/2006 | Rothman et al. | |
| 2006/0212123 A1 | 9/2006 | Lechmann et al. | |
| 2006/0235520 A1 | 10/2006 | Pannu | |
| 2006/0235526 A1 | 10/2006 | Lemaire | |
| 2006/0259143 A1 | 11/2006 | Navarro et al. | |
| 2006/0265072 A1 | 11/2006 | Richelsoph | |
| 2006/0282074 A1 | 12/2006 | Renaud et al. | |
| 2006/0287728 A1 | 12/2006 | Mokhtar et al. | |
| 2007/0010887 A1 | 1/2007 | Williams et al. | |
| 2007/0016217 A1 | 1/2007 | Dinville | |
| 2007/0016299 A1 | 1/2007 | Eckman | |
| 2007/0055378 A1 | 3/2007 | Ankney et al. | |
| 2007/0073403 A1 | 3/2007 | Lombardo et al. | |
| 2007/0073404 A1 | 3/2007 | Rashbaum et al. | |
| 2007/0088362 A1 | 4/2007 | Bonutti et al. | |
| 2007/0100454 A1 | 5/2007 | Burgess et al. | |
| 2007/0100455 A1 | 5/2007 | Parsons | |
| 2007/0100456 A1 | 5/2007 | Dooris et al. | |
| 2007/0149974 A1 | 6/2007 | Mangione | |
| 2007/0162130 A1 | 7/2007 | Rashbaum et al. | |
| 2007/0270951 A1 | 11/2007 | Davis et al. | |
| 2009/0216241 A1 | 8/2009 | Dinville | |
| 2012/0116466 A1 | 5/2012 | Dinville et al. | |

(56) References Cited

U.S. PATENT DOCUMENTS

| | | |
|---|---|---|
| 2013/0041408 A1 | 2/2013 | Dinville et al. |
| 2013/0253651 A1 | 9/2013 | Dinville |
| 2014/0214168 A1 | 7/2014 | Jodaitis et al. |
| 2014/0228885 A1 | 8/2014 | Dinville et al. |
| 2015/0051702 A1 | 2/2015 | Chataigner et al. |
| 2015/0080959 A1 | 3/2015 | Renaud et al. |
| 2015/0320568 A1 | 11/2015 | Ameil et al. |

FOREIGN PATENT DOCUMENTS

| | | |
|---|---|---|
| DE | 3023353 A1 | 4/1981 |
| DE | 8912648 U1 | 11/1990 |
| DE | 20310432 U1 | 9/2003 |
| DE | 20310433 U1 | 9/2003 |
| DE | 102004027986 A1 | 7/2005 |
| EP | 42271 A1 | 12/1981 |
| EP | 176728 A1 | 4/1986 |
| EP | 0298235 A1 | 1/1989 |
| EP | 0317972 A1 | 5/1989 |
| EP | 0333990 A2 | 9/1989 |
| EP | 0356112 A1 | 2/1990 |
| EP | 0512529 A1 | 11/1992 |
| EP | 0560141 A1 | 9/1993 |
| EP | 0566810 A1 | 10/1993 |
| EP | 0566810 B1 | 8/1996 |
| EP | 0738504 A1 | 10/1996 |
| EP | 0747025 A1 | 12/1996 |
| EP | 0852934 A1 | 7/1998 |
| EP | 0903126 A1 | 3/1999 |
| EP | 0955021 A1 | 11/1999 |
| EP | 0978258 A1 | 2/2000 |
| EP | 1222903 A1 | 7/2002 |
| EP | 1250898 A1 | 10/2002 |
| EP | 1344506 A1 | 9/2003 |
| EP | 1344508 A1 | 9/2003 |
| EP | 1374808 B1 | 12/2005 |
| EP | 1915111 A2 | 4/2008 |
| FR | 2124815 A5 | 9/1972 |
| FR | 2372622 A1 | 6/1978 |
| FR | 2659226 A1 | 9/1991 |
| FR | 2716619 A1 | 9/1995 |
| FR | 2718635 A1 | 10/1995 |
| FR | 2723841 A1 | 3/1996 |
| FR | 2724108 A1 | 3/1996 |
| FR | 2730159 A1 | 8/1996 |
| FR | 2737656 A1 | 2/1997 |
| FR | 2632516 A1 | 12/1999 |
| FR | 2787019 A1 | 6/2000 |
| FR | 2787021 A1 | 6/2000 |
| FR | 2824261 A1 | 11/2002 |
| FR | 2831796 A1 | 5/2003 |
| FR | 2843293 A1 | 2/2004 |
| FR | 2846550 A1 | 5/2004 |
| FR | 2865629 A1 | 8/2005 |
| FR | 2865630 A1 | 8/2005 |
| FR | 2869528 A1 | 11/2005 |
| JP | 2261446 A | 10/1990 |
| WO | WO-9011740 A1 | 10/1990 |
| WO | WO-1991007931 A1 | 6/1991 |
| WO | WO-9113598 A1 | 9/1991 |
| WO | WO-9301771 A1 | 2/1993 |
| WO | WO-9404100 A1 | 3/1994 |
| WO | WO-9909914 A1 | 3/1999 |
| WO | WO-1999053871 A1 | 10/1999 |
| WO | WO-9956675 A1 | 11/1999 |
| WO | WO-1999065412 A1 | 12/1999 |
| WO | WO-1999066864 A1 | 12/1999 |
| WO | WO-0053127 A1 | 9/2000 |
| WO | WO-0074606 A1 | 12/2000 |
| WO | WO-0101893 A1 | 1/2001 |
| WO | WO-0119295 A1 | 3/2001 |
| WO | WO-2001041680 A1 | 6/2001 |
| WO | WO-2001062191 A2 | 8/2001 |
| WO | WO-2002071960 A1 | 9/2002 |
| WO | WO-02089701 A2 | 11/2002 |
| WO | WO-2003015646 A2 | 2/2003 |
| WO | WO-03039400 A2 | 5/2003 |
| WO | WO-2003045262 A2 | 6/2003 |
| WO | WO-03059212 A1 | 7/2003 |
| WO | WO-03075804 A1 | 9/2003 |
| WO | WO-2003075803 A1 | 9/2003 |
| WO | WO-2004039291 A1 | 5/2004 |
| WO | WO-2004041129 A1 | 5/2004 |
| WO | WO-2004041131 A2 | 5/2004 |
| WO | WO-2004071360 A2 | 8/2004 |
| WO | WO-2005046534 A1 | 5/2005 |
| WO | WO-05074839 A1 | 8/2005 |
| WO | WO-05104996 A1 | 11/2005 |
| WO | WO-2005117728 A1 | 12/2005 |
| WO | WO-2006136760 A2 | 12/2006 |
| WO | WO-2007000654 A2 | 1/2007 |
| WO | WO-2007000654 A3 | 1/2007 |

OTHER PUBLICATIONS

"U.S. Appl. No. 10/476,565, Amendment After Final filed Nov. 29, 2007", 1 pg.

"U.S. Appl. No. 10/476,565, Response filed Nov. 6, 2007 to Final Office Action dated May 7, 2007", 37 pgs.

"European Application Serial No. 06779794.4, Office Action dated Aug. 5, 2009", 1 pg.

"France Application Serial No. 0213833, Preliminary Search Report dated Jul. 10, 2003", 2 pgs.

"France Application Serial No. 2730159, Preliminary Search Report dated Sep. 29, 1995", 1 pg.

"France Application Serial No. 2824261, Preliminary Search Report dated Feb. 25, 2002", 4 pgs.

"France Application Serial No. 2831796, Preliminary Search Report dated Aug. 2, 2002", 2 pgs.

"France Application Serial No. 2865629, Preliminary Search Report dated Sep. 14, 2004", 2 pgs.

"France Application Serial No. 2865630, Preliminary Search Report dated Jan. 12, 2005", 2 pgs.

"France Application Serial No. 2869528, Preliminary Search Report dated Dec. 13, 2004", 3 pgs.

"International Application Serial No. PCT/IB2006/001781, International Preliminary Report on Patentability dated Jul. 19, 2007", 6 pgs.

"International Application Serial No. PCT/IB2006/001781, International Search Report dated Mar. 22, 2007", 3 pgs.

"International Application Serial No. PCT/IB2006/001781, Written Opinion dated Mar. 22, 2007", 6 pgs.

"Request for Continued Examination in U.S. Appl. No. 11/051,710; dated Jul. 11, 2013", LDR Medical, by its attorneys; USPTO; Alexandria, Virgina, 3 pgs.

"USPTO OA of Feb. 18, 2009 in U.S. Appl. No. 11/632,253", 14 pgs.

Bouduk, N, et al., "A biological basis for instantaneous centres of rotation of the vertebral column", Proc institution Mechanical Engineers, (Jun. 16, 1995), 177-183.

Gertzban, S D, et al., "Centrode Patterns and Segmental Instability in Degenerative Disc Disease", BSc, M. Tile, MD, BSc, {Med), FRCS©, and B. Cruickshank, MD, FRCPath, Spine, vol. 10, No. 3 (Jan. 21, 1984), 257-261.

Griffith, S L, et al., "A Multicenter Retrospective Study of the Clinical Results of the LINK SB Charite Intervertebral Prosthesis", vol. 19, No. 16, (Mar. 21, 1994), 1842-1849.

Haher, T R, et al., "Instantaneous Axis of Rotation as a Function of the Three Columns of the Spine", MS, Spine, vol. 17, No. 6, (Jan. 09, 1992), S149-S154.

Haher, T R, et al., "The Effect of the Three Columns of the Spine on the Instantaneous Axis of Rotation in Flexion and Extension", Spine, vol. 16, No. 8, (Apr. 16, 1991), S312-S318.

Klein, J A, et al., "Relocation of the Bending Axis During Flexion-Extension of Lumbar Intervertebral Discs and its Implications for Prolapse", Spine, vol. 8, No. 6, (Nov. 18, 1982), 659-664.

Kostuik, J P, "Alternatives to Spinal Fusion", vol. 29, No. 4, (Oct. 4, 1998), 701-715.

(56) References Cited

OTHER PUBLICATIONS

Liu, X, et al., "A New Technique for the Three-Dimensional Study of the Spine in Vitro and In Vivo by Using a Motion-Analysis System", Journal of Spinal Disorders, vol. 10, No. 4, (Jan. 30, 1997), 329-338.
Pearcy, M J, et al., "Instantaneous Axes of Rotation of the Lumbar Intervertebral Joints", vol. 13, No. 9, (Nov. 15, 1987), 1033-1041.
Seligman, S D, "Computer Analysis of Spinal Segment Motion in Degenerative Disc Disease With and Without Axial Loading", Spine, vol. 9., No. 6, (Dec. 31, 1983), 566-573.
White Ill, A A, et al., "Clinical Biomechanics of the Spine", 2nd Edition, J.B. Lippincott Co., (1990), 128-130.
Yoshioka, T, et al., "Motion Characteristics of the Normal Lumbar Spine in Young Adults: Instantaneous of Axis of Rotation and Vertebral Center Motion Analysis", Journal of Spinal Disorders, vol. 3, No. 2, (1990), 103-113.
U.S. Appl. No 11/180,868, U.S. Pat. No 7.632,282, filed Jul. 13, 2005, Instrumentation and Methods for Insterting an Intervertebral Disc Prosthesis.
U.S. Appl. No. 12/435,955, U.S. Pat. No. filed May 5, 2009, Instrumentation and Methods for Inserting an Intervertebral Disc Prosthesis.
U.S. Appl. No. 13/892,933, U.S. Pat. No. 9,248,025 filed May 13, 2013, Instrumentation and Methods for Inserting an Intervertebral Disc Prosthesis.
"U.S. Appl. No. 10/476,565, Final Office Action dated May 7, 2007", 8 pgs.
"U.S. Appl. No. 10/476,565, Non Final Office Action dated Jul. 18, 2006", 9 pgs.
"U.S. Appl. No. 10/476,565, Notice of Allowance dated Nov. 29, 2007", 4 pgs.
"U.S. Appl. No. 10/476,565, Response filed Jan. 17, 2007 to Non Final Office Action dated Jul. 18, 2006 ", 23 pgs.
"U.S. Appl. No. 10/533,846, Final Office Action dated Oct. 15, 2008", 13 pgs.
"U.S. Appl. No. 10/533,846, Non Final Office Action dated Apr. 18, 2007", 11 pgs.
"U.S. Appl. No. 10/533,846, Non Final Office Action dated Dec. 26, 2007", 14 pgs.
"U.S. Appl. No. 10/533,846, Response filed Apr. 15, 2009 to Final Office Action dated Oct. 15, 2008", 13 pgs.
"U.S. Appl. No. 10/533,846, Response filed Jun. 25, 2008 to Non Final Office Action dated Dec. 25, 2007", 18 pgs.
"U.S. Appl. No. 10/533,846, Response filed Oct. 16, 2007 to Non Final Office Action dated Apr. 18, 2007", 16 pgs.
"U.S. Appl. No. 11/051,710, Appeal Brief filed Jan. 15, 2013", 27 pgs.
"U.S. Appl. No. 11/051,710, Final Office Action dated Jul. 20, 2010", 9 pgs.
"U.S. Appl. No. 11/051,710, Final Office Action dated Dec. 15, 2011", 9 pgs.
"U.S. Appl. No. 11/051,710, Non Final Office Action dated Apr. 11, 2011", 9 pgs.
"U.S. Appl. No. 11/051,710, Non Final Office Action dated Oct. 26, 2009", 12 pgs.
"U.S. Appl. No. 11/051,710, Notice of Allowance dated Apr. 11, 2013", 9 pgs.
"U.S. Appl. No. 11/051,710, Notice of Allowance dated Jun. 11, 2014", 6 pgs.
"U.S. Appl. No. 11/051,710, Response filed Jan. 20, 2011 to Final Office Action dated Jul. 20, 2011", 19 pgs.
"U.S. Appl. No. 11/051,710, Response filed Apr. 26, 2010 to Non Final Office Action dated Oct. 26, 2009", 19 pgs.
"U.S. Appl. No. 11/051,710, Response filed Oct. 11, 2011 to Non Final Office Action dated Apr. 11, 2011", 19 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Response filed Jan. 26, 2009 to Final Office Action dated Jul. 24, 2009", 9 pgs.
"U.S. Appl. No. 11/109,276, Response filed Apr. 16, 2008 to Non Final Office Action dated Oct. 16, 2007", 16 pgs.
"U.S. Appl. No. 11/109,276, Response filed Aug. 4, 2009 to Non Final Office Action dated Feb. 13, 2009", 4 pgs.
"U.S. Appl. No. 11/109,276, Response filed Aug. 6, 2007 to Non Final Office Action dated Feb. 6, 2007", 39 pgs.
"U.S. Appl. No. 11/180,868, Final Office Action dated Nov. 5, 2008", 10 pgs.
"U.S. Appl. No. 11/180,868, Non Final Office Action dated Jan. 22, 2008", 15 pgs.
"U.S. Appl. No. 11/180,868, Notice of Allowance dated Jul. 17, 2009", 5 pgs.
"U.S. Appl. No. 11/180,868, Notice of Allowance dated Jul. 31, 2009", 6 pgs.
"U.S. Appl. No. 11/180,868, Response filed May 5, 2009 to Final Office Action dated Nov. 5, 2008", 11 pgs.
"U.S. Appl. No. 11/180,868, Response filed Jul. 21, 2008 to Non Final Office Action dated Jan. 22, 2008", 15 pgs.
"U.S. Appl. No. 11/341,007, Non Final Office Action dated Apr. 13, 2009", 13 pgs.
"U.S. Appl. No. 11/676,237, Non Final Office Action dated Mar. 20, 2009", 10 pgs.
"U.S. Appl. No. 12/025,677, Final Office Action dated Jun. 29, 2012", 8 pgs.
"U.S. Appl. No. 12/025,677, Final Office Action dated Nov. 7, 2014", 12 pgs.
"U.S. Appl. No. 12/025,677, Non Final Office Action dated Feb. 19, 2014", 11 pgs.
"U.S. Appl. No. 12/025,677, Non Final Office Action dated Jun. 20, 2013", 8 pgs.
"U.S. Appl. No. 12/025,677, Non Final Office Action dated Oct. 7, 2011", 9 pgs.
"U.S. Appl. No. 12/025,677, Response filed Apr. 9, 2012 to Non Final Office Action date Oct. 7, 2011", 16 pgs.
"U.S. Appl. No. 12/025,677, Response filed May 6, 2015 to Final Office Action dated Nov. 7, 2014", 16 pgs.
"U.S. Appl. No. 12/025,677, Response filed Aug. 19, 2014 to Non Final Office Action dated Feb. 19, 2014", 23 pgs.
"U.S. Appl. No. 12/025,677, Response filed Dec. 20, 2013 to Non Final Office Action dated Jun. 20, 2013", 21 pgs.
"U.S. Appl. No. 12/025,677, Response filed Dec. 29, 2012 to Final Office Action dated Jun. 29, 2012", 20 pgs.
"U.S. Appl. No. 12/435,955, Final Office Action dated Jul. 23, 2012", 9 pgs.
"U.S. Appl. No. 12/435,955, Non Final Office Action dated Oct. 11, 2011", 8 pgs.
"U.S. Appl. No. 12/435,955, Notice of Allowance dated Jan. 26, 2013", 5 pgs.
"U.S. Appl. No. 12/435,955, Response filed Apr. 11, 2012 to Non Final Office Action dated Oct. 11, 2011", 12 pgs.
"U.S. Appl. No. 12/435,955, Response filed Dec. 24, 2012 to Final Office Action dated Jul. 23, 2012", 13 pgs.
"U.S. Appl. No. 13/892,933, Final Office Action dated Jul. 28, 2014", 7 pgs.
"U.S. Appl. No. 13/892,933, Non Final Office Action dated Jan. 2, 2014", 6 pgs.
"U.S. Appl. No. 13/892,933, Notice of Allowance dated Feb. 13, 2015", 6 pgs.
"U.S. Appl. No. 13/892,933, Notice of Allowance dated Sep. 14, 2015", 5 pgs.
"U.S. Appl. No. 13/892,933, Response filed Apr. 2, 2014 to Non Final Office Action dated Jan. 2, 2014", 10 pgs.
"U.S. Appl. No. 13/892,933, Response filed Dec. 29, 2014 to Final Office Action dated Jul. 28, 2014", 11 pgs.
"European Application Serial No. 05702425.9, Communication Pursuant to Article 94(3) EPC dated Mar. 2, 2009", 3 pgs.

(56) References Cited

OTHER PUBLICATIONS

"European Application Serial No. 05702425.9, Notice of Intention to Grant dated Oct. 22, 2010", 35 pgs.

"European Application Serial No. 05702425.9, Response filed Jul. 22, 2009 to Communication Pursuant to Article 94(3) EPC dated Mar. 2, 2009", 16 pgs.

"European Application Serial No. 06779794.4, Communication Pursuant to Article 94(3) EPC dated Nov. 10, 2010", 6 pgs.

"European Application Serial No. 06779794.4, Notice of Intention to Grant dated Jan. 19, 2009", 55 pgs.

"European Application Serial No. 06779794.4, Response filed Mat 11, 2009 to Notice of Intention to Grant dated Jan. 19, 2009", 33 pgs.

"European Application Serial No. 06779794.4, Response filed May 19, 2011 to Communication Pursuant to Article 94(3) EPC dated Nov. 10, 2010", 21 pgs.

"International Application Serial No. PCT/162002/002998, International Preliminary Examination Report dated Dec. 22, 2003", 8 pgs.

"International Application Serial No. PCT/162002/002998, International Search Report dated Sep. 16, 2003", 6 pgs.

"International Application Serial No. PCT/1B2002/004642, International Preliminary Examination Report dated Apr. 1, 2004", 4 pgs.

"International Application Serial No. PCT/1B2002/004642, International Search Report dated Jul. 2, 2003", 2 pgs.

"International Application Serial No. PCT/1B2003/004872, International Preliminary Examination Report dated Mar. 1, 2005", 6 pgs.

"International Application Serial No. PCT/1B2003/004872, International Search Report dated Mar. 3, 2004", 3 pgs.

"International Application Serial No. PCT/162005/000280, International Search Report dated Jun. 24, 2005", 5 pgs.

"International Application Serial No. PCT/1B2005/001151, International Search Report dated Sep. 12, 2005", 3 pgs.

"International Application Serial No. PCT/162005/00280, International Preliminary Report on Patentability dated Jan. 16, 2006", 8 pgs.

"International Application Serial No. PCT/162005/00280, Written Opinion dated Jun. 24, 2005", 8 pgs.

"International Application Serial No. PCT/1B2006/01781, International Preliminary Report on Patentability dated Jul. 19, 2007", 6 pgs.

"International Application Serial No. PCT/1B2006/01781, International Search Report dated Mar. 22, 2007", 3 pgs.

"International Application Serial No. PCT/1B2006/01781, Written Opinion dated Mar. 22, 2007", 6 pgs.

\* cited by examiner

INSTRUMENTATION AND METHODS FOR INSERTING AN INTERVERTEBRAL DISC PROSTHESIS

CROSS REFERENCE TO RELATED APPLICATIONS

This application is a continuation of U.S. patent application Ser. No. 13/892,933, filed May 13, 2013, and issuing as U.S. Pat. No. 9,248,025 on Feb. 2, 2016, which is a continuation of U.S. patent application Ser. No. 12/435,955, filed May 5, 2009, and issuing as U.S. Pat. No. 8,439,931 on May 14, 2013, which is a continuation of U.S. patent application Ser. No. 11/180,868, filed Jul. 13, 2005, and issuing as U.S. Pat. No. 7,632,282 on Dec. 15, 2009, which claims priority under 35 U.S.C. 119 to French Patent Application No. 05 06652, filed in FRANCE on Jun. 29, 2005.

TECHNICAL FIELD

The present invention relates to instrumentation for inserting intervertebral disc prostheses.

BACKGROUND OF THE INVENTION

Various types of instruments for inserting intervertebral disc prostheses are known, such as those disclosed in the French patent application FR0405899000 filed by the applicant. These instruments only allow insertion by anterior access, along the antero-posterior axis of the prosthesis. Preparation of the vertebrae between which the prosthesis is to be implanted by this type of instrumentation therefore requires opening the tissue covering these vertebrae and pushing aside the blood vessels on the anterior face of the spinal column, which generates a risk for the patient.

The embodiments disclosed herein provide instrumentation and methods that allow insertion of a prosthesis between the vertebrae, laterally or obliquely, while appropriately positioning the prosthesis in relation to the sagittal plane and the coronal plane.

Embodiments of instrumentation for the insertion of intervertebral disc prosthesis between vertebrae in accordance with the present invention comprise a guide and at least one separator. In preferred embodiments, the guide has at least two lateral faces, at least one upper plate, at least one lower plate, at least one retainer, a cage defining an insertion axis for the intervertebral disc prosthesis and having open posterior and anterior faces, and an angle adjuster adapted to adjust the angle formed by the insertion axis and an antero-posterior median sagittal axis of the vertebrae. The separators are sized to maintain a gap between the upper vertebra and the lower vertebra that is sufficient for insertion of the intervertebral disc prosthesis through the guide into the intervertebral space. For the disclosed embodiments, during the insertion of the intervertebral disc prosthesis the upper plate is disposed proximal to a plane substantially coincident with the lower surface of the upper vertebra, and the lower plate is disposed proximal to a plane substantially coincident with the upper surface of the lower vertebra. The upper plate and the lower plate are separated by a distance approximately equal to the height of the intervertebral disc prosthesis. The angle adjuster is adapted to position the guide opposite the intervertebral space between the upper vertebra and the lower vertebra and to adjust an angle formed by the insertion axis and an antero-posterior median sagittal axis defined by the intersection of a midline, substantially vertical, sagittal plane and a transverse, substantially horizontal, plane of the spinal column.

According to another feature in an embodiment, the angle adjuster comprises at least one sighting device configured for visual adjustment of the angle between the insertion axis and the antero-posterior median sagittal axis.

According to another feature in an embodiment, the angle adjuster comprises a sighting device configured for operation with at least one pin implanted into at least one of the upper vertebra and the lower vertebra and approximately oriented with the antero-posterior median sagittal axis of said vertebra to align said sighting device with the antero-posterior median sagittal axis.

According to another feature in an embodiment, the instrumentation further comprises:

at least one pin for implantation into at least one of the upper vertebra and the lower vertebra in approximate orientation with the antero-posterior median sagittal axis of said vertebra;

at least one offset adjuster adjustably linking the angle adjuster to the at least one pin.

According to another feature in an embodiment, the instrumentation further comprises:

at least one contact adjuster disposed approximately parallel to the insertion axis;

a coupling between the at least one contact adjuster and the angle adjuster allowing movement of the angle adjuster with respect to the at least one contact adjuster;

a connector configured to move along the longitudinal axis of the pin and to connect the at least one offset adjuster to the at least one pin.

According to another feature in an embodiment, the at least one pin comprises a sharp point.

According to another feature in an embodiment, the angle adjuster comprises at least one adjustment gauge indicating at least one parameter concerning the position of the guide relative to the vertebrae.

According to another feature in an embodiment, the adjustment gauge comprises a lateral offset gauge comprising a pointer pointing to graduations indicating the lateral offset of the guide from the antero-posterior median sagittal axis of the vertebrae.

According to another feature in an embodiment, the adjustment gauge comprises an angle gauge comprising a pointer pointing to radial graduations indicating the angle between the insertion axis of the intervertebral disc prosthesis and the antero-posterior median sagittal axis of the vertebrae.

According to another feature in an embodiment, the instrumentation further comprises a tightener that selectively allows or prevents rotation of the angle adjuster with respect to the guide, thereby permitting adjustment and fixation of the angle between the insertion axis of the intervertebral disc prosthesis and the antero-posterior median sagittal axis.

According to another feature in an embodiment, the at least one retainer comprises at least one groove permitting the at least one separator to slide within the groove.

According to another feature in an embodiment, the at least one retainer comprises at least one shaft providing at least one axis of rotation for the at least one separator.

According to another feature in an embodiment, the guide further comprises a stop limiting the rotation of the at least one separator about the at least one axis of rotation.

According to another feature in an embodiment, the rotation of an at least one separator is limited by an adjustable stop enabling to set the extent to which the rotation is limited.

According to another feature in an embodiment, the guide comprises at least one channel oriented substantially parallel to the insertion axis of the intervertebral disc prosthesis and configured to guide at least one part protruding from at least one surface of the intervertebral disc prosthesis.

According to another feature in an embodiment, the insertion axis of the intervertebral disc prosthesis through the guide is oriented approximately parallel to a longitudinal centerline of the guide passing through the open anterior and posterior faces of the cage.

According to another feature in an embodiment, the insertion axis of the intervertebral disc prosthesis through the guide is not oriented approximately parallel to a longitudinal centerline of the guide passing through the open anterior and posterior faces of the cage.

According to another feature in an embodiment, the instrumentation further comprises at least one chisel having at least one blade and suitable shape and dimension for engagement with the guide and for cutting at least one notch in a vertebra.

According to another feature in an embodiment, the chisel comprises a shaft, a handle at the end of the shaft opposite the at least one blade, and an adjustable stop limiting the travel of the chisel inside the guide.

According to another feature in an embodiment, the chisel comprises two blades and a spacer of suitable dimension to separate the blades by a distance approximately equal to the height of the intervertebral space.

According to another feature in an embodiment, the instrumentation further comprises an impactor having a shaft, a handle at one end of the shaft for manipulating the impactor, and at the other end of the shaft a pusher having shape and dimensions substantially conforming to at least one edge of the intervertebral disc prosthesis contacted by the pusher during use.

According to another feature in an embodiment, the impactor has an adjustable stop limiting the travel of the impactor inside the guide.

According to another feature in an embodiment, the instrumentation further comprises a holder for the intervertebral disc prosthesis and wherein the guide comprises a recess providing clearance for holder for the intervertebral disc prosthesis sufficient to position the intervertebral disc prosthesis into the guide.

According to another feature in an embodiment, the instrumentation further comprises a holder for the guide engaging at least two notches of the guide.

According to another feature in an embodiment, the holder for the guide is configured to engage the at least two notches of the guide without interfering with engagement of a recess of the guide by tools for accessing the intervertebral space or by the holder for the intervertebral disc prosthesis.

Methods for inserting intervertebral disc prostheses between two vertebrae are also provided.

General steps for preparing the vertebral site for insertion of an intervertebral disc prosthesis between two vertebrae are known, and are not an aspect of the inventive method disclosed herein. In general, such preparatory steps comprise removal of the natural biological intervertebral disc, clearing the intervertebral space, and maintaining a gap between the upper vertebra and lower vertebra with a known instrument.

Methods for inserting an intervertebral disc prosthesis in accordance with the present invention can be performed using instrumentation comprising at least one pin and a guide having at least one upper plate, at least one lower plate, a cage defining an insertion axis for the intervertebral disc prosthesis and having open posterior and anterior faces, and an angle adjuster. In a preferred embodiment, a method according the present invention comprises:

implanting at least one pin in the median sagittal axis of one of the two vertebrae;

measuring the dimensions of the intervertebral space;

choosing the intervertebral disc prosthesis to be implanted;

choosing the guide to be used;

adjusting the angle adjuster based on an antero-posterior median sagittal axis of the spinal column, defined by the intersection of a midline, substantially vertical, sagittal plane and a transverse, substantially horizontal, plane of the spinal column, on the dimensions of the intervertebral space and on the obstacles to access to the intervertebral space, in order to set a desired angle between the insertion axis for the intervertebral disc prosthesis and the antero-posterior median sagittal axis;

positioning the guide adjacent to the intervertebral space at the desired angle;

inserting the intervertebral disc prosthesis into the guide through the open posterior face of the cage; and inserting the intervertebral disc prosthesis into the intervertebral space through the open anterior face of the cage.

According to another feature in an embodiment, the method further comprises a step of adjusting an offset adjuster for setting a lateral offset of the guide relative to the antero-posterior median sagittal axis.

According to another feature in an embodiment, the step of inserting the intervertebral disc prosthesis into the intervertebral space is performed using an impactor comprising a shaft and an adjustable stop, said step further comprising adjustment of the stop and the application of a thrust to the impactor.

According to another feature in an embodiment, the step of adjusting the angle adjuster is performed using a sighting device for aligning the guide with the antero-posterior median sagittal axis, said step further comprising placement of the sighting device in contact with the at least one pin.

According to another feature in an embodiment, the method further comprises a step of adjusting an offset adjuster of adjustable length connecting the angle adjuster of the guide to a connector connected to the pin, this adjusting step being implemented thanks to the measurements of the intervertebral space.

According to another feature in an embodiment, the step of positioning the guide adjacent to the intervertebral space further comprises translation of the guide along an axis substantially parallel to the antero-posterior median sagittal axis until the guide is proximal to the vertebrae.

According to another feature in an embodiment, the method further comprises the insertion of one or more separators into the intervertebral space.

According to another feature in an embodiment, the method further comprises the engagement of at least one of the one or more separators with at least one retainer of the guide.

According to another feature in an embodiment, the step of positioning the guide is performed with a holder for the guide.

According to another feature in an embodiment, the step of inserting the intervertebral disc prosthesis into the guide is performed with a holder for the intervertebral disc prosthesis, the guide comprising a recess providing clearance sufficient for the holder for the intervertebral disc prosthesis to position the intervertebral disc prosthesis into the guide.

According to another feature in an embodiment, the step of positioning the guide is performed with a holder for the guide configured to engage at least two notches of the guide to provide clearance for tools for accessing the intervertebral space.

According to another feature in an embodiment, the method further comprises, before inserting the intervertebral disc prosthesis into the intervertebral space, the step of preparing the intervertebral space using a chisel having at least one blade, an adjustable stop and suitable shape and dimension for engagement with the guide and for cutting at least one notch in at least one vertebra.

According to another feature in an embodiment, the method further comprises the step of clearing the intervertebral space of the bone debris generated by cutting the notch.

According to another feature in an embodiment, the method further comprises a step of removing the guide, the one or more separators, and the at least one pin after the step of inserting the intervertebral disc intervertebral disc prosthesis into the intervertebral space.

Other features and advantages of the invention will become clearer upon reading the following description of various embodiments with reference to the attached drawings.

BRIEF DESCRIPTION OF THE FIGURES

FIG. 7B presents further details of FIG. 7A.

DESCRIPTION OF EMBODIMENTS

Figure 1:
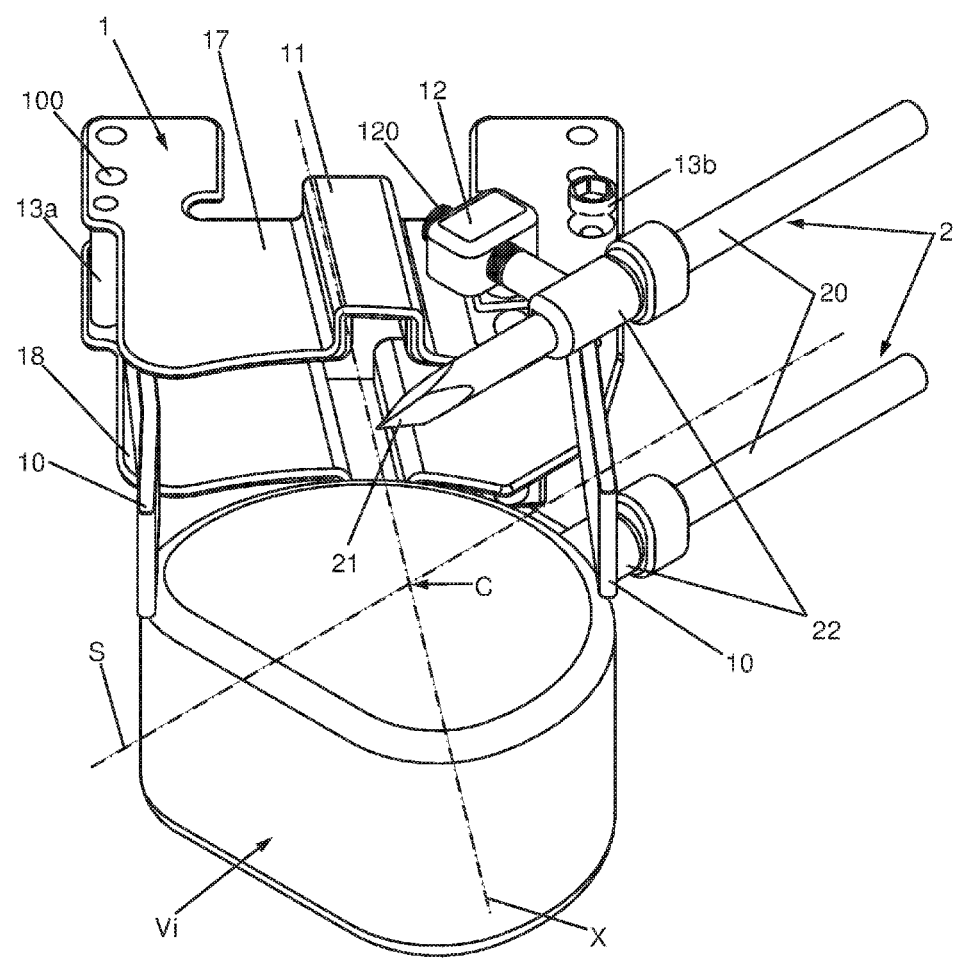
FIG. 1 represents a perspective view of the instrumentation according to an embodiment of the invention, with a pin implanted in a vertebra and the guide facing the intervertebral space located above this vertebra.

The invention relates to an instrumentation and methods for inserting intervertebral disc prostheses (P) between vertebrae (Vi, Vs). The invention complements general surgical instruments and methods. The following description presents different, non-restrictive, embodiments of devices and methods according to various features of the invention. The different structures and steps in the various embodiments can be incorporated in the other embodiments in various combinations.

In a preferred embodiment, the instrumentation comprises a guide (1) in the shape of an open cage that can slide, by use of a movable connector (22), on at least one pin (2) implanted into a vertebra. Two pins (2), one implanted in upper vertebra (Vs) and the other implanted in the lower vertebra (Vs), and two movable connectors (22), can also be used.

Various elements of the embodiments described herein involve an antero-posterior reference axis (S). The determination of this antero-posterior reference axis will be apparent to the surgeon using the embodiments of the instrumentation and methods described. In general, the antero-posterior reference axis will lie along the intersection of a plane substantially coincident with a median sagittal (a substantially vertical plane along the midline of the spine) and a plane substantially coincident with a horizontal plane (a transverse plane, along the antero-posterior axis of the vertebrae and substantially horizontal), although other orientations may be appropriate depending on the particular characteristics of the spine and vertebrae and/or on the choice of the surgeon. For example, the antero-posterior reference axis (S) may not lie along the midline sagittal plane of the spine and may thus be Para-Sagittal and it can be inclined leftward or rightward in the antero-posterior direction of the vertebrae. The antero-posterior reference axis (S) may also not be aligned along the horizontal plane of the vertebrae and may thus be inclined upward or downward in the antero-posterior direction of the vertebrae.

A holder (not represented) for the guide can be used to place the guide (1) over the pin (2) and to make it slide until it is proximal with the vertebrae. In a preferred embodiment, the guide (1) comprises two lateral faces, at least one upper plate (17) and at least one lower plate (18) which together form a cage intended to receive the prosthesis (P) through its open posterior face and allow the insertion through its open anterior face of the prosthesis (P) between the lower (Vi) and upper (Vs) vertebrae. In use of the instrumentation, separators (10), comprising, for example, substantially rectangular plates having dimensions adapted to the height of the prosthesis (P) (generally without regard to any osteal anchors), are placed approximately parallel to the lateral faces of the guide (1) and in proximity to the lateral faces. Separators (10) maintain a sufficient gap between the vertebrae and, co-operating with the guide (1), allow the insertion of the prosthesis (P) between the vertebrae. A holder (not represented) of the prosthesis (P) allows placement of the prosthesis (P) inside the guide (1). An impactor (4) is provided for pushing the prosthesis (P) through the open cage of the guide into the intervertebral space.

Figure 3:
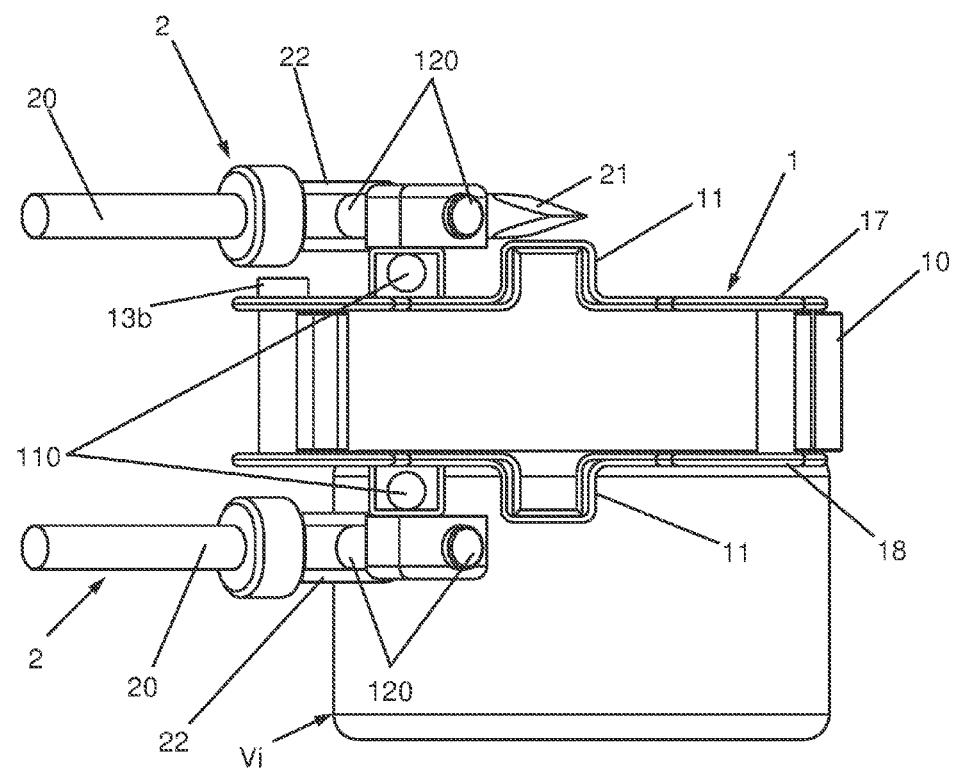
FIG. 3 represents a side view of the instrumentation in FIG. 1, seen from the posterior face of the guide.
Figure 4A:
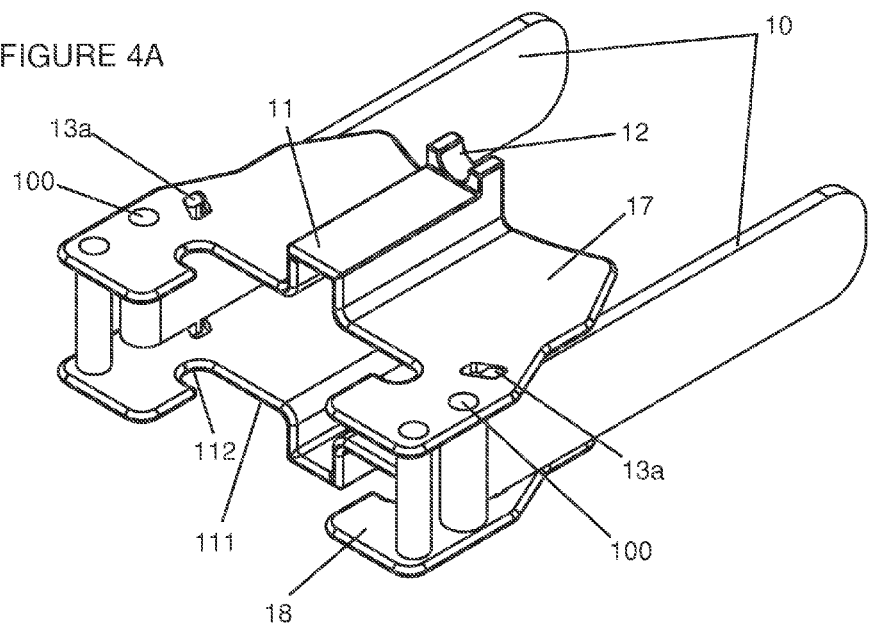
FIGS. 4A and 4B represent, respectively, a perspective view and a top view of the guide according to an embodiment of the invention.
Figure 4B:
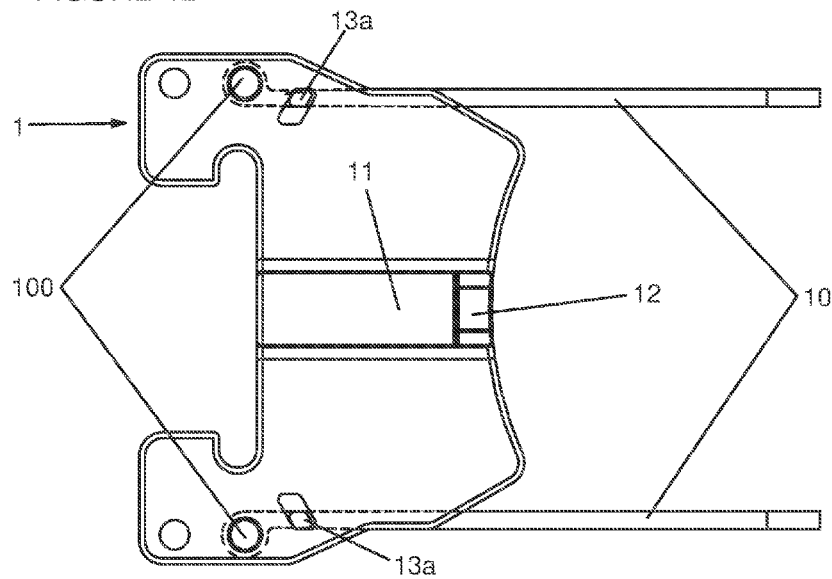

Various embodiments of the invention will now further be described in detail in reference to the drawings. As shown in FIGS. 1 and 3, the guide (1) has a cage through which the prosthesis will be inserted until it reaches the intervertebral space. The cage is open on its anterior and posterior faces. The guide (1) comprises lateral faces, at least one upper plate (17) and at least one lower plate (18). In the embodiments represented in the drawings, the guide (1) has a shape substantially of a parallelepiped, with its upper plate (17) and lower plate (18) approximately parallel to each other. In an alternative embodiment (not represented), the upper plate (17) and lower plate (18) are not approximately parallel to each other and the guide (1) has, in coronal (frontal) section, a substantially trapezoidal shape. In this alternative embodiment, the separators (10) could, according to the insertion angle (A1) of the prosthesis (P), comprise non-rectangular plates such as trapezoidal plates, and/or could have different dimensions from one lateral face of the guide (1) to the other. A trapezoidal embodiment is especially suitable for implanting a prosthesis having upper and lower surfaces form an angle, thus imposing an inclination on the vertebrae between which they are intended to be implanted.

Figure 5A:
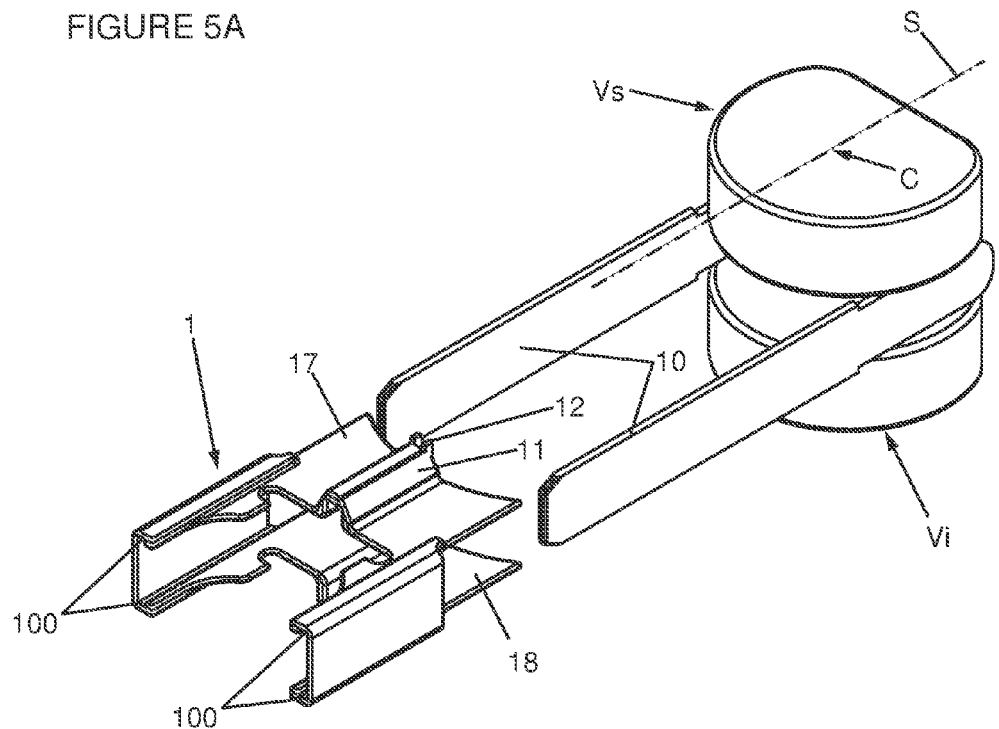
FIGS. 5A and 5B represent perspective views of another embodiment of the guide of the instrumentation, respectively, before and after the introduction of the separating elements in the guide.
Figure 5B:
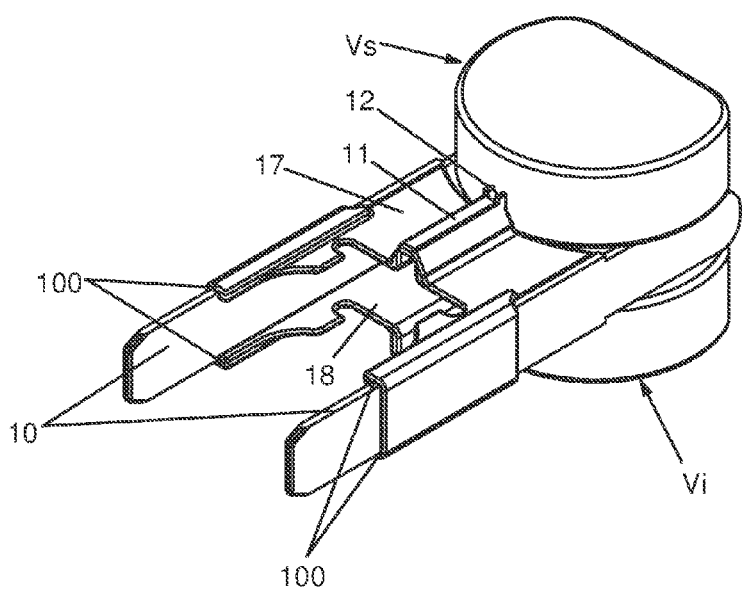

In the embodiment represented in FIGS. 5A and 5B, the guide (1) has solid lateral faces comprising substantially rectangular plates, whereas in the embodiments represented in the other figures, the lateral faces of the guide are open and comprise rods linking the upper plate (17) and lower plate (18). However, as mentioned above, the different structures described for the various embodiments of the instruments of the invention can be adapted to other instruments and/or other embodiments. Thus, the guide (1) could have open lateral faces in the embodiment represented in FIGS. 5A and 5B or even have solid lateral faces in the embodiments represented in the other figures.

Figure 11A:
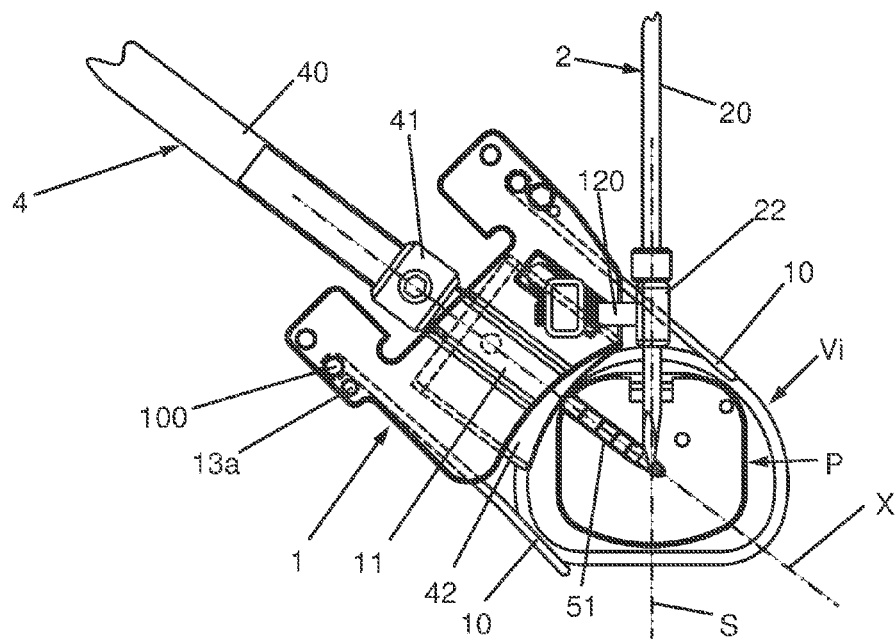
FIG. 11A represents a transparent view of the instrumentation according to an embodiment of the invention, when the prosthesis is being pushed into the intervertebral space by the impactor according to an embodiment of the invention.
Figure 11B:
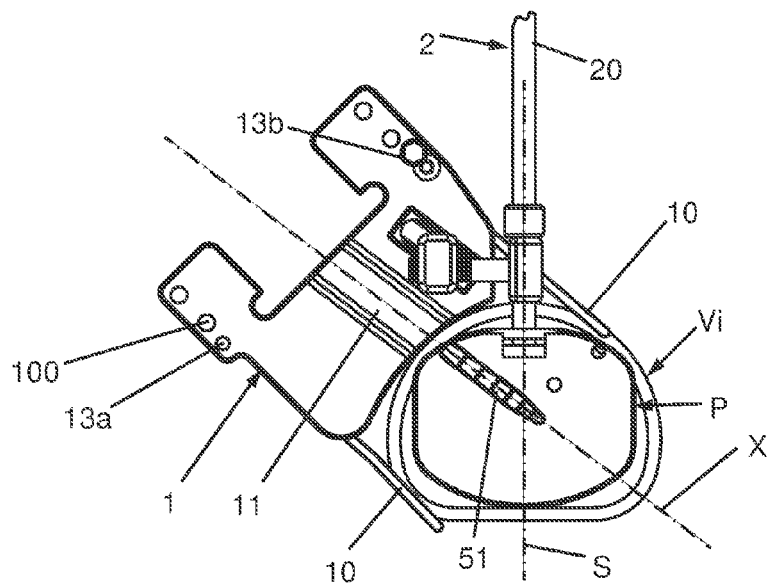
FIG. 11b represents a prosthesis in place in the intervertebral space after the impactor has been removed.

The guide (1) comprises, proximate to its lateral faces, retainer (100) allowing it to co-operate with separators (10) used to maintain a gap between the vertebrae before and during the insertion of the prosthesis. The separators (10) have a shape and dimensions adapted to the height of the prosthesis (P) (generally without regard to any osteal anchors), allowing for maintenance of a sufficient gap between the vertebrae (Vi, Vs) for the introduction of the prosthesis (P) into the intervertebral space. The height of the cage of the guide (1) is adapted to the height of the prosthesis (generally without regard to any osteal anchors). Guides of different heights generally will be used for prostheses of different heights. The width of the cage of the guide (1), however, can be configured to allow the same guide to be used for the implanting of prostheses of substantially different widths, as for the two prostheses represented in FIGS. 11A and 11B. When a guide (1) is used for prostheses of substantially different widths, preferred embodiments use guiding channels (11) engaging osteal anchors on the prostheses to guide the prostheses during insertion. A surgeon, however, will preferably use a guide (1) having a size most suitable to the dimensions of and the encumbrances of access to the intervertebral space, and will implant a prosthesis having a size most suitable to the dimensions of the guide (1) and the intervertebral space.

In the embodiments represented in FIGS. 5A and 5B, the retainer (100) of the guide (1) comprises grooves on each of the lateral edges of each of the lower (18) and upper (17) plates of the guide (1). The grooves receive the separators (10), and permit the separators (10) to co-operate with the guide (1) by sliding in the grooves (100). The sliding of the separators (10) in relation to these retainers (100) allows a translation of the guide (1) in relation to the separators (10). Thus, the separators (10) could be inserted between the vertebrae (Vs, Vi) before or after the positioning of the guide (1). For example, this embodiment also allows to remove the guide (1) once the prosthesis has been implanted, while leaving the separators (10) in place between the vertebrae (Vs, Vi) to allow proper positioning of the prosthesis.

Figure 2:
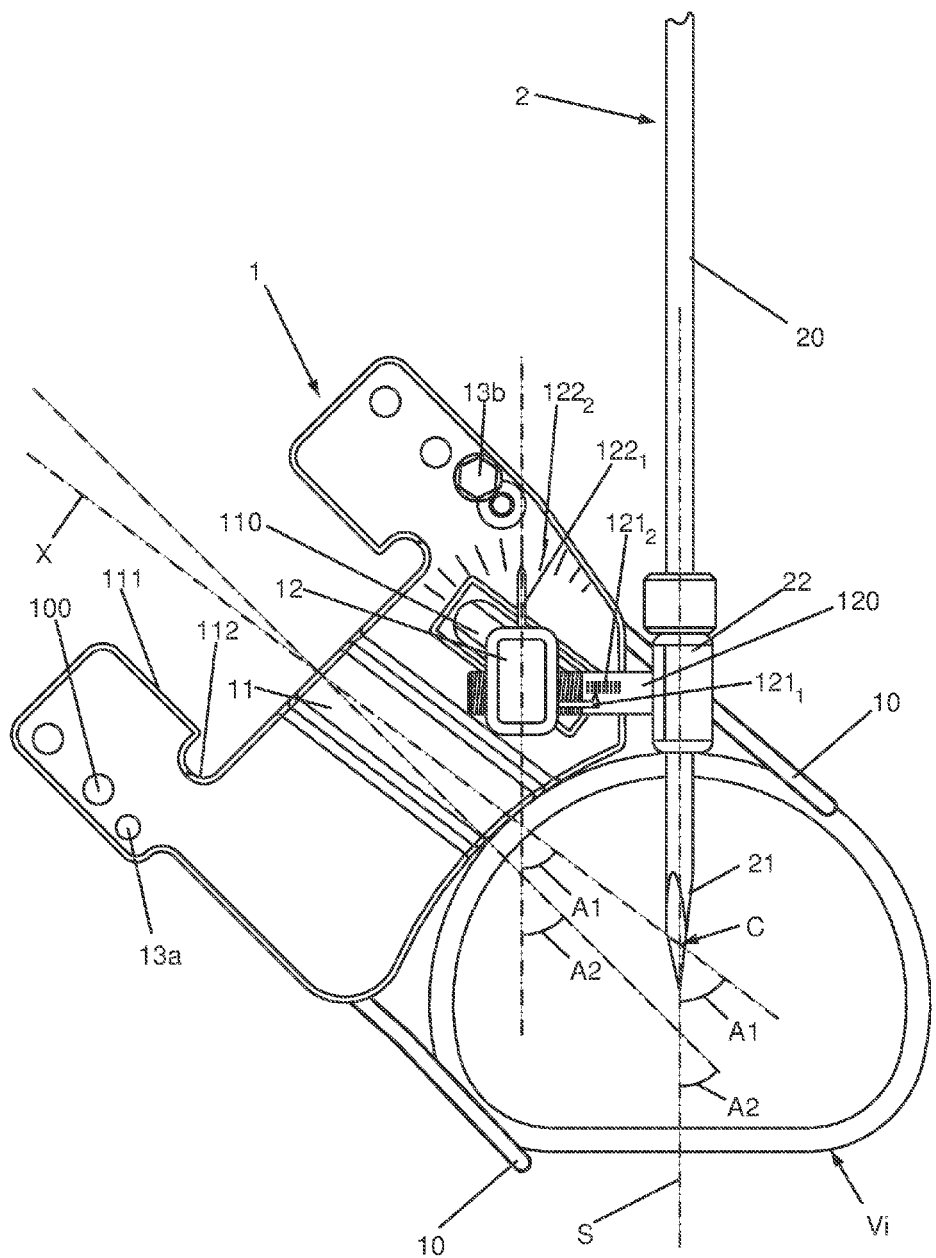
FIG. 2 represents a top view of the instrumentation represented in FIG. 1.

In the embodiments represented in FIGS. 1 to 4 and 7 to 11, the retainer (100) of the guide comprises shafts located proximally to the lateral faces of the guide (1). These shafts provide axes of rotation about which the separators (10) may rotate. In these embodiments of retainer (100), as seen in FIGS. 1 and 2 stops limiting the rotation can be disposed proximal to the lateral faces, towards the exterior of the guide, limiting rotation of the separators (10) about their respective axis of rotation (100). In a preferred embodiment, these stops comprise a rod (13a) having a distance to the anterior face of the guide (1) that is less than the distance of the axis of rotation (100) of the separators (10) to the anterior face of the guide (1). In another embodiment, the stops are adjustable and comprise, for example, at least one conical part (13b) screwed into at least the upper (17) or lower (18) plates of the guide. The depth of the adjustable stop can be set using the screw threads, and will adjust the limit on the rotation of the separators (10) about their axis of rotation (100). The stops limiting the rotation of the separators (10) about their axis of rotation can also comprise, as in the embodiment represented in FIGS. 4A and 4B, studs (13a) attached to the separators (10) and projecting into an opening or recess made in at least one of the lower plate (18) and upper plate (17). In this embodiment of stops (13a), the relative sizes of these studs and the opening or recess can be used to establish the limit on the rotational freedom of the separators (10).

In a preferred embodiment, instrumentation according to the invention comprises at least a pin (2) having a sharp point (21) intended to be implanted into an antero-posterior reference axis (S) of one of the vertebrae (Vi, Vs) between which the prosthesis (P) is to be implanted. Implanting the pin (2) into a vertebra provides a reference that, in conjunction with other structure of the guide (1), permits targeting the point (C) onto which the prosthesis (P) is to be centred in the intervertebral space. The guide (1) comprises at least one angle adjuster (12) allowing adjustment of the insertion axis (X) of the prosthesis (P) in relation to the antero-posterior reference axis (S) of the vertebrae, and thus the angle (A1) between the insertion axis (X) and the antero-posterior reference axis (S). The intersection between the insertion axis (X) and the antero-posterior reference axis (S) defines a point which can be set to coincide with the point (C) onto which the prosthesis (P) is to be centred in the intervertebral space. The antero-posterior reference axis (S) may lie along the intersection of a plane substantially coincident with a median sagittal plane and a plane substantially coincident with a horizontal plane, although other orientations may be appropriate depending on the particular characteristics of the spine and vertebrae and/or depending on the choice of the surgeon.

In the embodiments represented in FIGS. 4A, 4B, 5A and 5B, the angle adjuster (12) comprises a sighting device having, for instance, a back sight intended to cooperate with at least one pin (2) implanted in the median sagittal axis of at least one vertebra. The back sight preferably has a suitable shape and dimension to cooperate with the pin (2) to allow the back sight to be placed against the pin and to slide the guide (1) along the pin, thereby permitting a suitable positioning of the guide (1) along the antero-posterior reference axis (S). By providing stable placement of the guide (1) with reference to the antero-posterior reference axis (S), the sighting device (12) also facilitates adjustment (either visually or by use of a gauge or other device) of the angle (A1) between the insertion axis (X) of the prosthesis (P) and the antero-posterior reference axis (S) of the vertebrae (Vi, Vs).

In the embodiments represented in FIGS. 1 to 3 and 7 to 11, an offset adjuster (120) of adjustable length links the angle adjuster (12) to a connector (22) that can slide on pin (2). For one embodiment, the offset adjuster (120) comprises a rod with one end fixed to the connector (22) and the opposite end threaded to mate with a treaded hole in the angle adjuster (12). In another of the various alternative embodiments, the offset adjuster (120) comprises a rod attached to connector (22) but freely rotatable with respect to connector (22). In such alternative embodiment, offset adjuster (120) can be screwed in the threaded hole in angle adjuster (12) even when connector (22) is in place on pin (2). For example, a six-sided hole can be formed in the threaded end of offset adjuster (120) and used to rotate offset adjuster (120) with known tools.

The guide (1) can also comprise at least one contact adjuster (110). In various embodiments of contact adjusters (110), the contact adjuster (110) is disposed approximately parallel to the insertion axis (X) of the prosthesis (P). The angle adjuster (12) is configured to slide along the contact adjuster (110), although other adjustable couplings between the angle adjuster (12) and the contact adjuster (110) are readily apparent. In this arrangement, angle adjuster (12) can be set to the desired angle (A1) between the insertion axis (X) of the prosthesis (P) and the antero-posterior reference axis (S), and by adjusting the distance between angle adjuster (12) and connector (22) using offset adjuster (120), the intersection point between the insertion axis (X) of the prosthesis (P) and the antero-posterior reference axis (S) of the vertebrae can be made to coincide with the point (C) on which the prosthesis (P) is to be centered. By moving the angle adjuster (12) along the contact adjuster (110), the guide (1) can be brought proximal to the vertebrae (Vi, Vs) while maintaining the connector (22) in the desired proximity to the adjacent vertebra.

In various embodiments, the angle adjuster (12) of the guide (1) comprises an adjustment gauge. The adjustment gauge can be configured to indicate one or more adjustment of the guide (1), including, for example, the angle (A1) between the insertion axis (X) of the prosthesis (P) and the antero-posterior reference axis (S) and/or the length of the offset distance between angle adjuster (12) and connector (22).

The adjustment gauge embodiment illustrated in FIG. 2 comprises a lateral offset gauge. In this embodiment, the lateral offset gauge indicates the length of the offset distance between angle adjuster (12) and connector (22), indirectly measuring the offset of the guide (1) laterally from the antero-posterior reference axis (S). The lateral offset gauge comprises a pointer ($121_1$) attached to the angle adjuster (12) and located proximal to graduations ($121_2$) made in a surface of the offset adjuster (120). The position of the pointer ($121_1$) in relation to the graduations ($121_2$) indicates the length of the offset distance between angle adjuster (12) and connector (22) and therefore the lateral offset of the guide (1) in relation to the pin (2).

The adjustment gauge embodiment illustrated in FIG. 2 further comprises an angle gauge indicating the angle (A1) between the insertion axis (X) of the prosthesis (P) and the antero-posterior reference axis (S). In this embodiment, the angle gauge comprises a pointer ($122_1$) attached to the angle adjuster (12) and located proximal to radial graduations ($122_2$) made in the surface of the guide (1). The position of the pointer ($122_1$) in relation to the graduations ($122_2$) indicates the angle (A1) along which the prosthesis (P) will be implanted in relation to the antero-posterior reference axis (S) of the vertebrae (Vs, Vi).

In an alternative embodiment, a tightener is provided that selectively allows or prevents rotation of the angle adjuster (12) with respect to the cage of the guide (1). The tightener permits adjustment of the angle (A1) between the insertion axis (X) of the prosthesis (P) and the antero-posterior reference axis (S) by allowing rotation of the angle adjuster (12), and permits fixation of that angle (A1) in proper adjustment by preventing rotation of the angle adjuster (12).

In the disclosed embodiments, the pin (2) is intended to be implanted in a horizontal transverse plane of the vertebrae. Two pins (2) can also be used, along with two angle adjuster (12), for example, placed one on one of the upper plate (17) and one on the lower plate (18) as shown in FIG. 3. However, the instrumentation also may use a pin (2) to be implanted other than in a horizontal transverse plane of the vertebrae. For example, the pin (2) may be implanted in an inclined manner in the sagittal plane with its point (21) oriented towards the bottom of the spinal column. In that configuration, the guide (1) could be provided with a single angle adjuster (12) on one of the upper plate (17) or lower plate (18), but still be held in the suitable horizontal position by using to the adjustable offset adjuster (120) and the angle adjuster (12).

Some prostheses have osteal anchors (51) on the surfaces that contact adjacent vertebrae. For example, winglets on the prosthesis can be provided to engage notches made in the surfaces of the vertebrae. The surfaces of the vertebrae engaged by the osteal anchors (51) of this type of prosthesis therefore must be prepared before insertion of the prosthesis. Accordingly, in a preferred embodiment the instrumentation comprises a chisel (3) used to prepare intervertebral space. The chisel (3) has suitable shape and dimension to penetrate into the open cage of the guide (1) and pass through the guide (1) to make cuttings on the vertebrae that will be engaged by an osteal anchor (51). In a preferred embodiment, at least one plate among the upper (17) and lower (18) plates of the guide (1) comprises a guiding channel (11) oriented along the insertion axis (X) of the prosthesis (P). This guiding channel (11) has a shape and dimensions adapted to the shape and dimensions of an osteal anchor (51) of the prosthesis (P). The notch made in the vertebra using the chisel (3) assists centering of the prosthesis in relation to the point (C). In the embodiments represented in the drawings, the guiding channel (11) defining the insertion axis (X) of the prosthesis is not approximately parallel to the longitudinal centerline (L) passing through the anterior and posterior open faces of the guide (1), but the guiding channel (11) can obviously be made so as to define an insertion axis (X) of the prosthesis approximately parallel to the longitudinal centerline passing through the anterior and posterior faces of the guide (1).

Figure 6A:
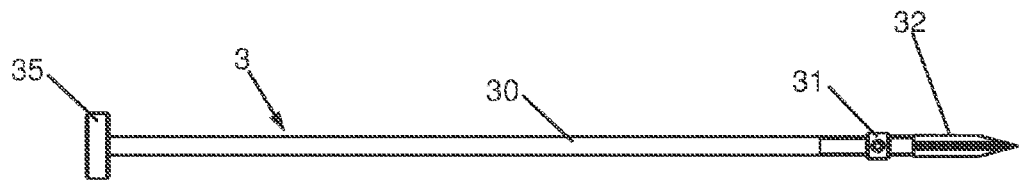
FIGS. 6A and 6B represent, respectively, a top view and a side view of the chisel according to an embodiment of the invention.
Figure 6B:
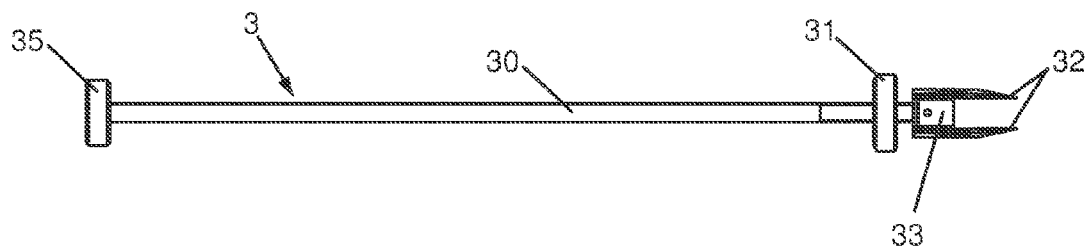

In a preferred embodiment, the chisel (3) comprises a shaft (30) having, at one of its ends, at least one blade (32) of suitable shape and dimension for engagement with the guiding channel (11) of the guide (1) and for cutting a notch in a vertebra complementary with the shape and dimension of an osteal anchor (51). The shaft has, at its other end, a handle (35) allowing positioning of the blade (32) into the guiding channel (11) manipulating of the chisel to make a notch in the vertebra for the osteal anchor (51) of the prosthesis (P). An adjustable stop (31) on the shaft (30) can limit the travel of the chisel (3) in the axis (X) of the guide (1) and therefore limit the length of the notch, which can correspond to length of the osteal anchor (51). In the embodiment in FIGS. 6A and 6B, the chisel (3) comprises two blades (32) held apart from each other by a spacer (33) of suitable dimension to separate the blades (32) by a distance approximately equal to the height of the intervertebral disc prosthesis (P) (generally without regard to any osteal anchors). Using two guiding channels (11), the chisel (3) can be used to simultaneously form two notches of suitable dimensions and positions to receive the osteal anchors (51) assembled on the upper and lower surfaces of the prosthesis (P).

Figure 6C:
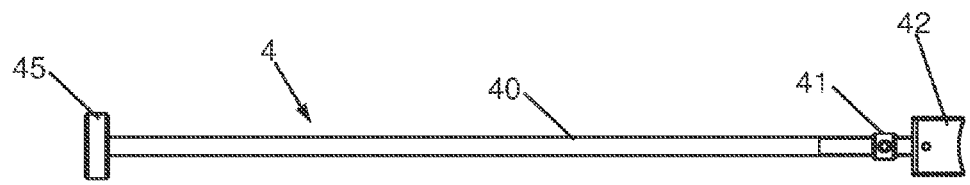
FIGS. 6C and 6D represent, respectively, a top view and a side view of the impactor on an embodiment of the invention.
Figure 6D:
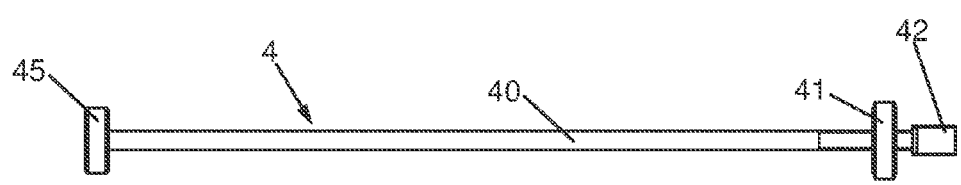
Figure 7A:
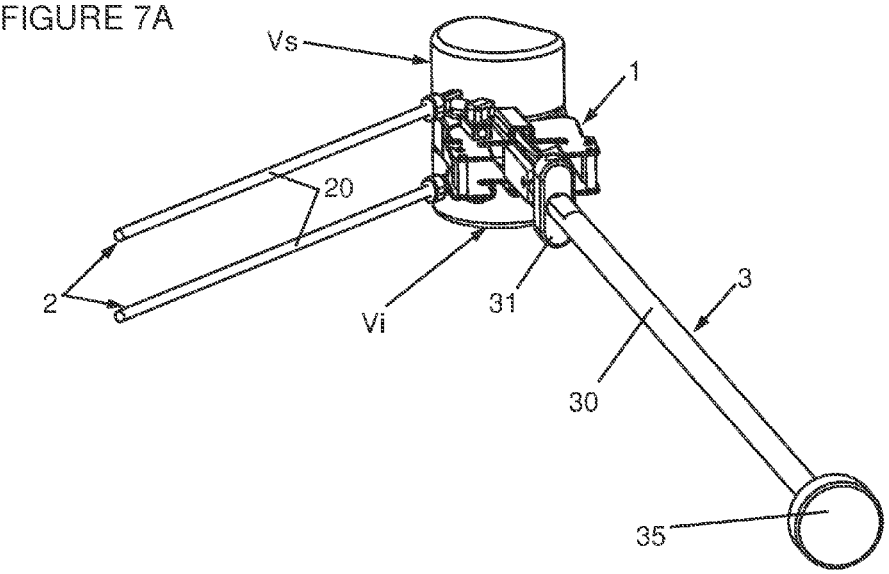
FIGS. 7A and 7B represent a perspective view of an embodiment of the invention, when using a chisel.
Figure 7B:
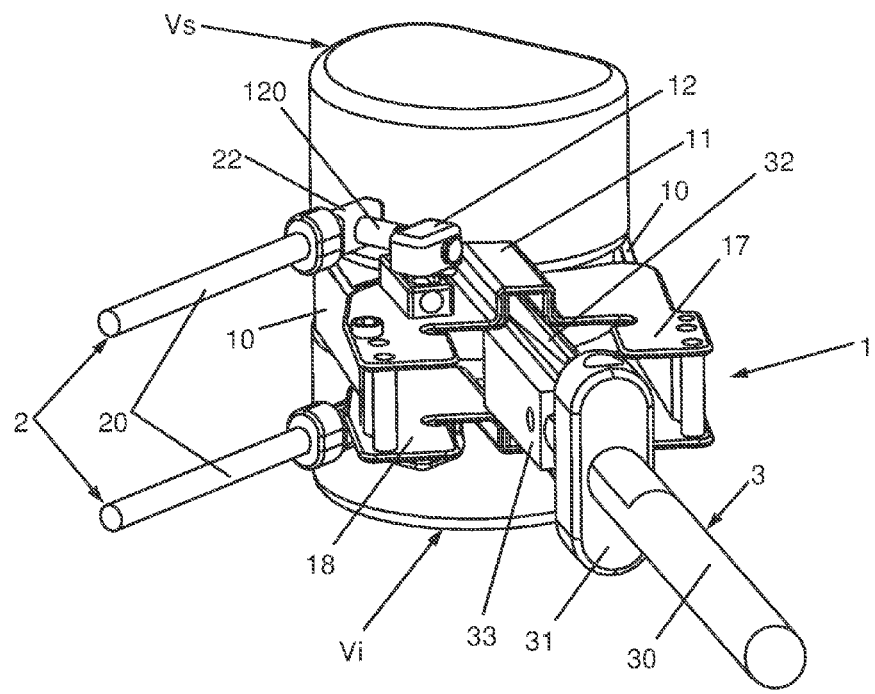
Figure 8A:
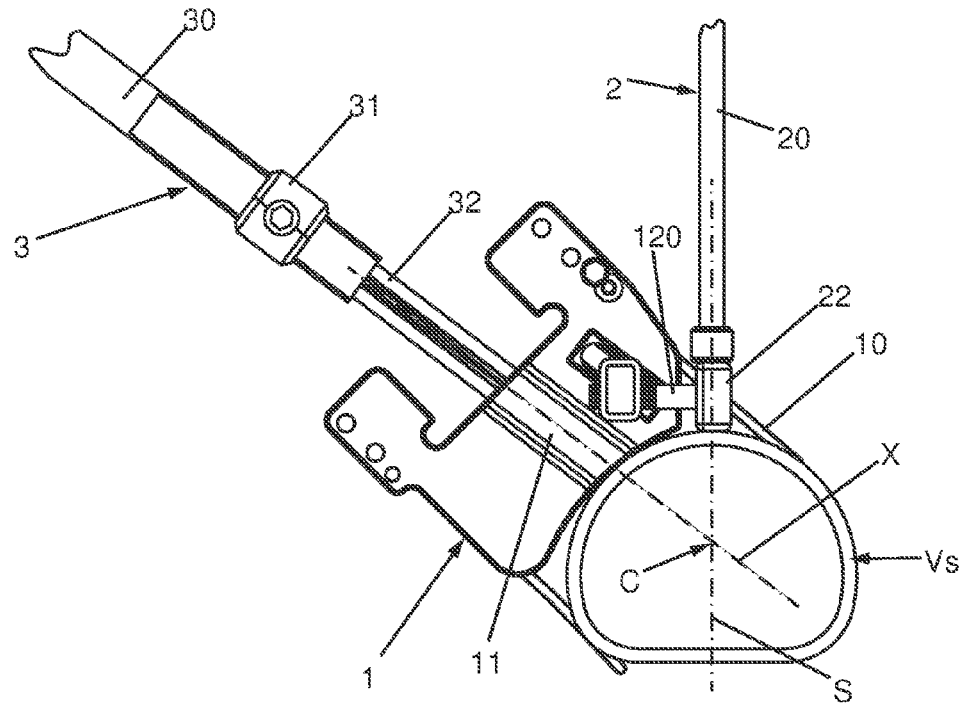
FIGS. 8A and 8B represent a top view of the instrumentation according to an embodiment of the invention, when using the chisel and, respectively, before and after the penetration of the chisel into the vertebra.
Figure 8B:
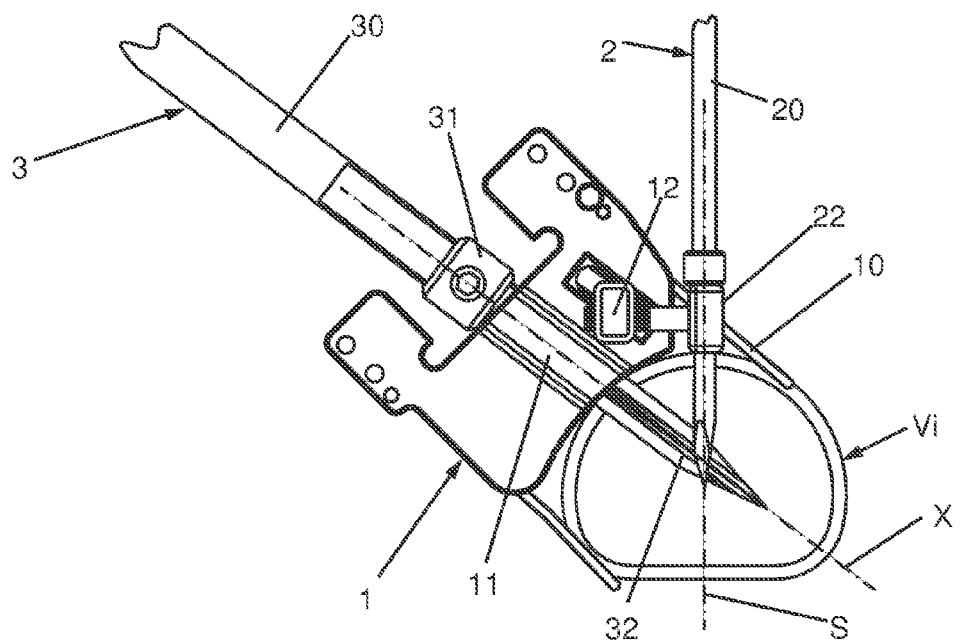
Figure 9A:
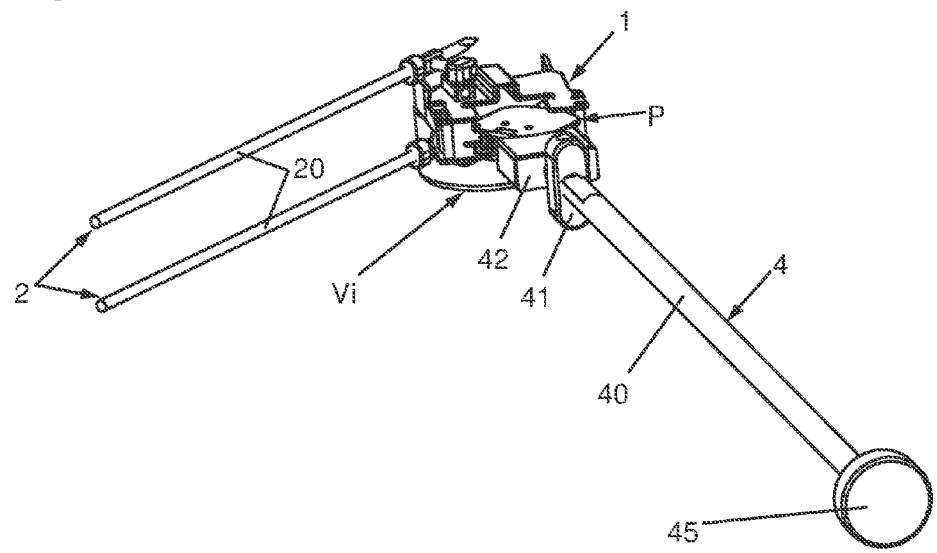
FIG. 9A represents a perspective view of the instrumentation according to an embodiment of the invention, when using the impactor.
Figure 9B:
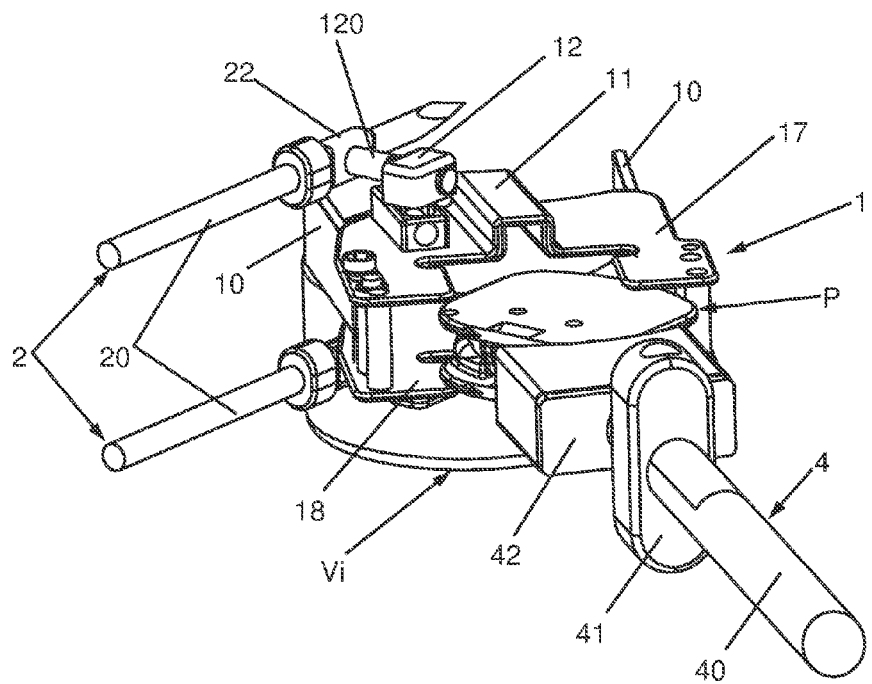
FIG. 9B presents further details of FIG. 9A.
Figure 10A:
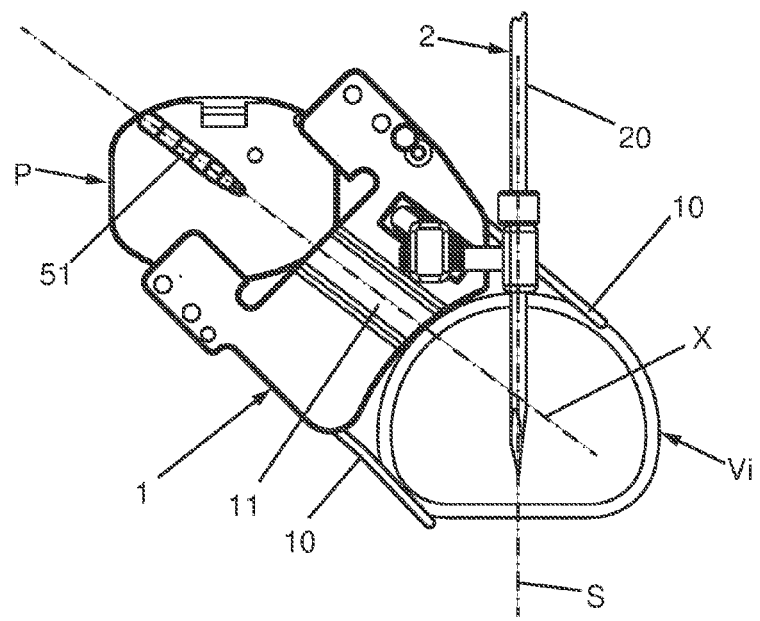
FIG. 10A represents a top view of the instrumentation according to an embodiment of the invention, during the insertion of the prosthesis in the guide.
Figure 10B:
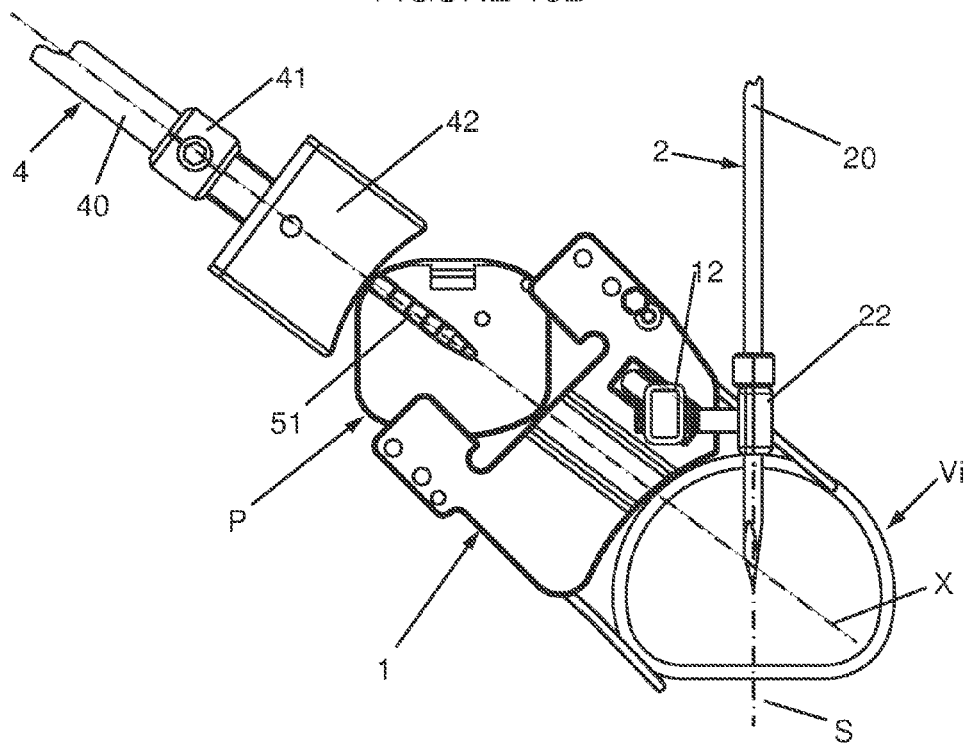
FIG. 10B represents a top view of the instrumentation according to an embodiment of the invention, when using the impactor pushing the prosthesis inside the guide.

In an embodiment of the invention, the instrumentation comprises an impactor (4) as shown in FIGS. 6C and 6D used to move the prosthesis (P) through the cage of the guide (1) into the intervertebral space. The impactor (4) comprises a shaft (40), a handle (45) at one end of the shaft for manipulating the impactor, and at the other end of the shaft a pusher (42) having shape and dimensions substantially conforming to the edges of the intervertebral disc prosthesis (P) contacted by the pusher (42) during use. The height and width of the pusher (42) can be substantially equal, respectively, to the height (generally without regard to any osteal anchors) and the width of the prosthesis (P). An adjustable stop (41) on the shaft (40) of the impactor (4) can limit the travel of the impactor (4) in the insertion axis (X) of the prosthesis (P) and therefore control the depth to which the prosthesis (P) will be inserted into the intervertebral space. The stop (41) therefore can assist centering the prosthesis (P) in relation to the point (C).

In an embodiment of the invention, the instrumentation can comprise a holder (not shown) for the prosthesis (P). As shown in the drawings, at least one of the upper plate (17) and the lower plate (18) comprises a recess (111) providing clearance of the holder for the prosthesis (P) and allowing the prosthesis (P) to be placed in the guide (1) with the holder. Such holder for the prosthesis (P) may consist, for example, of forceps or pliers or tweezers of a known type, with shape and dimensions adapted to insert the prosthesis (P) in the guide (1) by engaging the recess (111).

In an embodiment of the invention, the instrumentation can comprise a holder (not shown) for the guide (1). The holder can assist positioning the guide (1) in suitable position in contact with the vertebrae (Vi, Vs). The holder co-operates with at least two notches (112) made on at least one of the upper plate (17) and the lower plate (18). As represented in drawings, the notches (112) are located in the recess (111) of the guide (1). Such holder for the guide (1) may consist, for example, of dilating forceps or opening pliers, or opening tweezers of a known type, with shape and dimensions adapted to co-operate with the notches (112) while leaving the recess (111) accessible to forceps or pliers or suitable tools for accessing the intervertebral space. For example, the holder for the guide (1) may consist of opening pliers having opening ends curved in a direction approximately orthogonal to the direction of the opening of the pliers. These curved ends thus co-operate with the notches (112) in the recess (111) and may have dimensions adapted so that, when they co-operate with the notches (112), they do not substantially protrude from the notches (112) inside the recess (111). Such holder will thus hold the guide (1) while leaving a recess (111) accessible for the clearance of pliers or small tweezers or any suitable tools for accessing the intervertebral space through the guide (1). The recess (111) may also be accessible for the clearance of the holder for the prosthesis (P) and for the positioning of the prosthesis (P) into the guide (1), if the holder has still not been removed at this step.

The various embodiments of the invention described above provide instrumentation for implanting an intervertebral disc prosthesis (P) between the vertebrae (Vs, Vi). The use of the instrumentation will now be described, providing detail of the steps taken to implant the prosthesis.

As aforementioned, the invention compliments general surgical instruments and methods, which are not an aspect of the inventive method disclosed herein and will not be described. In addition, the prerequisite steps for preparing the patient and access to the vertebrae, for example from the anterior face, will not be described in detail. Prior to the implanting itself of the prosthesis (P), the surgeon creates an access to the vertebrae and removes the fibro-cartilaginous tissue of the natural biological intervertebral disc. Generally, separators (tweezers, according to a commonly used designation) of a known type maintain a gap between the vertebrae during the removal of the natural biological disc by the surgeon. The natural gap of the vertebrae will have been measured beforehand to determine the height (generally without regard to any osteal anchors) of the prosthesis (P) to be implanted in the intervertebral space and, consequently, the height of the guide (1) that is to be chosen for implantation. Measuring the height of the intervertebral space also allows determination of the height of the separators (10), which is chosen to maintain the gap required for inserting the prosthesis (P) between the vertebrae. The guide (1) will thus be chosen according to the height of these separators (10) and the dimensions of the prosthesis (P) in the horizontal plane, which will depend on the dimensions of the vertebrae and the encumbrances to accessing the intervertebral space.

During the removal of the natural biological disc by the surgeon, separators (tweezers) commonly used are too cumbersome for the rest of the operation and are thus replaced by a wedge (called "spacer" or "bougie", according to a commonly used designation in English or French, respectively) whose height will have been chosen so as to preserve the natural gap of the vertebrae and to correspond to the height of the prosthesis (P) (generally without regard to any osteal anchors).

The removal of the natural biological intervertebral disc can be preceded or followed by a step of implanting at least one pin (2) of the instrumentation in at least one of the vertebrae (Vi, Vs) between which the prosthesis is to be implanted. So that the pin (2) provides a symmetrical reference in relation to the vertebrae, the implanting of the pin (2) is performed by placing it, preferably horizontally, along the antero-posterior reference axis (S) of the vertebra. The dimensions of the guide (1) chosen for implanting the prosthesis will affect the height in the vertebra for implantation of pin (2), which should enable the angle adjuster (12) to place the guide (1) opposite the intervertebral space with its upper plate (17) and lower plate (18) in contact with the respectively upper and lower surfaces of the respectively upper and lower vertebrae. In a known manner, the surgeon measures the exact dimensions of the vertebrae, using a known measuring device. The measuring of the vertebrae, notably along the antero-posterior axis, informs the surgeon of the depth of the intervertebral space and allows the surgeon to determine the ideal dimensions of the prosthesis (P) in the horizontal plane and to calculate, as a function of the dimensions of the measured vertebrae and of the chosen prosthesis, the position of the point (C) on which the prosthesis (P) is to be centered. By taking a radiograph of the vertebra in which the pin (2) was implanted, for example using a known image intensifier, the surgeon can also control the proper positioning of the point (21) of the pin in the vertebra, for example its alignment on the median sagittal axis. The pins (2) are short and comprise, for example, small diameter rods. The small dimensions of the pins allow the surgeon to possibly recommence the step of implanting the pin (2) into the vertebra if he considers that the position of the point (21) is unsatisfactory.

Once these measurements have been made, the surgeon has all the information necessary to choose the most appropriate guide (1) and prosthesis (P). According to the embodiment of the guide (1) chosen by the surgeon, the surgeon adjusts, according to the gathered measurements, the angle adjuster (12) to accurately target the point (C) on which the prosthesis (P) is to be centered in the intervertebral space.

The positioning of the guide (1) opposite the intervertebral space can be performed using a holder for the guide or without the use of such a holder. Among other embodiments of the invention, the surgeon can choose between separators (10) that slide in the grooves of the retainer (100) or separators (10) that rotate about their axes of rotation on shafts (100). For separators (10) that slide in the grooves of the retainer (100), the surgeon inserts separators (10) in the intervertebral space, removes the known wedge (bougie or spacer), and slides the guide (1) on the separators (10) to bring the guide (1) proximal to the vertebrae. For separators (10) that rotate about their axes of rotation on shafts (100), the surgeon inserts the separators (10) assembled on shafts (100), removes the known wedge (bougie or spacer), and drives the separators (10) into the intervertebral space until the guide is proximal with the vertebrae.

The surgeon may choose different embodiments of the angle adjuster (12) to more readily facilitate placement of the prosthesis (P) centered at point (C). According to the encumbrance of the surgeon's access to the vertebrae, the surgeon will choose one of the embodiments described below so as to insert the prosthesis along the antero-posterior sagittal axis or along an inclined axis.

In the embodiment of the instrument described above in which the angle adjuster (12) comprise a sighting device created by a back sight, and preferably in the case where the prosthesis can be implanted straight on and does not require an oblique insertion, the surgeon targets the point (C) by placing the sighting device in the median sagittal axis of the vertebrae marked by at least one pin (2) implanted in at least one vertebra. The back sight preferably has a suitable shape and dimension to co-operate with the pin (2), so as to allow the back sight to be placed against the pin and to slide the guide (1) along the pin, thereby ensuring suitable positioning of the guide in relation to the vertebrae. The surgeon inserts the prosthesis (P) it into the cage of the guide (1) though the cage's open posterior face. A holder for the prosthesis can be used that allows, as mentioned above, insertion of the prosthesis (P) into the cage of the guide while the holder for the guide is still in its place and holding the guide in contact with the vertebrae. The impactor (4) allows the surgeon to implant the prosthesis between the vertebrae by pushing on the handle (45) of the impactor (4) or by hitting, for example with a hammer, on this handle (45). The adjustable position of the stop (41) on the shaft (40) of the impactor (4) will have already been set according to the distance of point (C) on which the prosthesis is to be centred between the vertebrae, in relation to the anterior face of the vertebrae. The adjusting of the position of the stop naturally takes into account the size of the pusher (42) of the impactor (4) and the diameter of the prosthesis (P).

According to the vertebrae (Vi, Vs) between which the prosthesis (P) is to be implanted, implanting of the prosthesis (P) along the antero-posterior sagittal axis may not necessarily be the easiest or least risky solution. For example, the vena cava and the aorta, which are major life-supporting blood vessels, pass in front of the lumbar vertebrae and considerably encumber the access to the anterior face of such vertebrae. The surgeon may therefore prefer to implant the intervertebral disc prosthesis (P) along an oblique axis of insertion, such as an antero-lateral axis in the case of access to the vertebrae from the anterior face. Some of the embodiments of the invention facilitate insertion of the prosthesis (P) obliquely, for example, by use of an angle adjuster (12) to set an angle (A1) between the insertion axis (X) of the prosthesis and the antero-posterior reference axis (S).

The small diameter pins (2) can be implanted in the median sagittal plane of the vertebrae without having to shift to any great extent the tissue and/or the organs passing over the anterior face of the vertebrae. The angle (A1) created between the insertion axis (X) of the prosthesis and the antero-posterior reference axis (S), as well as the magnitude of the offset of the guide (1) on one side of the vertebrae, will already have been determined according to the encumbrances to access to the vertebrae (Vi, Vs), the size of the vertebrae (Vi, Vs), and the size of the prosthesis (P). Thus, adjusting the angle (A1) and the offset of guide (1) from the antero-posterior reference axis (S) permits the intersection the axis of insertion (X) and of the antero-posterior reference axis (S) to coincide with the point (C) on which the prosthesis is to be centred.

Offset adjuster (120) can be used to establish the offset of guide (1) from the antero-posterior reference axis (S), for example, by screwing to a greater or lesser degree a threaded end of offset adjuster (120) into a threaded hole made in the angle adjuster (12). As mentioned above, adjustment of the length of the offset adjuster (120) can be performed before or after the connector (22) is placed on the pin (2), depending on the chosen embodiment. The sliding of the connector (22) over the pin (2) allows the guide (1) to be brought proximal to the vertebrae, with its anterior face opposite the intervertebral space. Other steps for implanting can be identical to those previously described, for example by using the impactor (4) of which the position of the stop (41) on the shaft (40) of the impactor (4) will already have been set according to the distance of the point (C) in relation to the anterior face of the vertebrae and according to the size of the prosthesis (P).

If the prosthesis comprises osteal anchors (51) fixed to the surfaces of the prosthesis (P), the chisel (3) is used to make notches in the vertebrae of shape and dimension complementary with the shape and dimension of the osteal anchors (51). The handle (35) of the chisel (3) can be used to push, or perhaps use strikes of a hammer, and pull the chisel (3) to make such notches. As mentioned above, the shape and dimension of the different embodiments of the chisel (3) are adapted to the type of prosthesis (P) to be implanted and to the type of osteal anchors (51). After preparing the intervertebral space with the chisel (3), the surgeon removes the chisel (3) from the inside of the guide (1) and removes the fragments of bone generated by making the notches. The prosthesis is implanted between the vertebrae using the impactor (4).

Once the prosthesis has been properly placed in the intervertebral space, the surgeon removes the guide (1), the separators (10) and the pin(s) (2).

Although the present invention has been described in detail, it will be apparent to those skilled in the art that many embodiments taking a variety of specific forms and reflecting changes, substitutions and alterations can be made without departing from the spirit and scope of the invention. Therefore, the described embodiments illustrate but do not restrict the scope of the claims.

The invention claimed is:

1. Instrumentation for inserting an intervertebral disc prosthesis into an intervertebral space between an upper vertebra and a lower vertebra, the instrumentation comprising:
    a guide comprising at least one retainer,
    a cage defining an insertion axis for the intervertebral disc prosthesis and having open posterior and anterior faces, and
    an angle adjuster adapted to position the guide opposite the intervertebral space and to adjust an angle formed by the insertion axis and an antero-posterior reference axis, the angle adjuster including an adjustment gauge to visually indicate at least the angle formed by the insertion axis and an antero-posterior reference axis.

2. Instrumentation of claim 1 in which the angle adjuster comprises at least one sighting device configured for visual adjustment of the angle between the insertion axis and the antero-posterior reference axis.

3. Instrumentation of claim 1 in which the angle adjuster comprises a sighting device configured for operation with at least one pin implanted into at least one of the upper vertebra and the lower vertebra and approximately oriented with the antero-posterior reference axis of said vertebra to align said sighting device with the antero-posterior reference axis.

4. Instrumentation of claim 1 further comprising:
    at least one pin for implantation into at least one of the upper vertebra and the lower vertebra in approximate orientation with the antero-posterior reference axis of said vertebra; and
    at least one offset adjuster adjustably linking the angle adjuster to the at least one pin.

5. Instrumentation of claim 4 further comprising:
    at least one contact adjuster disposed approximately parallel to the insertion axis;
    a coupling between the at least one contact adjuster and the angle adjuster allowing movement of the angle adjuster with respect to the at least one contact adjuster; and
    a connector configured to move along the longitudinal axis of the pin and to connect the at least one offset adjuster to the at least one pin.

6. Instrumentation of claim 5 in which the at least one pin comprises a sharp point.

7. Method for implanting an intervertebral disc prosthesis into an intervertebral space between two vertebrae comprising the steps of:
    acquiring instrumentation comprising at least one pin, a guide, a cage defining an insertion axis for the intervertebral disc prosthesis and having open posterior and anterior faces, and an angle adjuster;
    implanting at least one pin in at least one of the two vertebrae, along an antero-posterior reference axis;
    measuring the dimensions of the intervertebral space;
    choosing the intervertebral disc prosthesis to be implanted;
    choosing the guide to be used;
    adjusting the angle adjuster based on the antero-posterior reference axis, on the dimensions of the intervertebral space and on the obstacles to access to the intervertebral space, in order to set a desired angle between the insertion axis for the intervertebral disc prosthesis and the antero-posterior reference axis;
    positioning the guide adjacent to the intervertebral space at the desired angle;
    inserting the intervertebral disc prosthesis into the guide through the open posterior face of the cage; and
    inserting the intervertebral disc prosthesis into the intervertebral space through the open anterior face of the cage.

8. Method for implanting of claim 7 further comprising a step of adjusting an offset adjuster for setting a lateral offset of the guide relative to the antero-posterior reference axis.

9. Method for implanting of claim 7 in which the step of inserting the intervertebral disc prosthesis into the intervertebral space is performed using an impactor comprising a shaft and an adjustable stop, said step further comprising adjustment of the stop and the application of a thrust to the impactor.

10. Method for implanting of claim 7 in which the step of adjusting the angle adjuster is performed using a sighting device for aligning the guide with the antero-posterior reference axis, said step further comprising placement of the sighting device in contact with the at least one pin.

11. Method for implanting of claim 7 further comprising a step of adjusting an offset adjuster of adjustable length connecting the angle adjuster of the guide to a connector connected to the pin, this adjusting step being implemented thanks to the measurements of the intervertebral space.

12. Method for implanting of claim 11 further comprising a step of removing the guide, the one or more separators, and the at least one pin after the step of inserting the intervertebral disc intervertebral disc prosthesis into the intervertebral space.

13. Method for implanting set forth in claim 7 in which the step of positioning the guide adjacent to the intervertebral space further comprises translation of the guide along an axis substantially parallel to the antero-posterior reference axis until the guide is proximal to the vertebrae.

14. Method for implanting of claim 7 further comprising the insertion of one or more separators into the intervertebral space.

15. Method for implanting of claim 14 further comprising the engagement of at least one of the one or more separators with at least one retainer of the guide.

16. Method for implanting of claim 7 in which the step of positioning the guide is performed with a holder for the guide.

17. Method for implanting of claim 7 in which the step of inserting the intervertebral disc prosthesis into the guide is performed with a holder for the intervertebral disc prosthesis, the guide comprising a recess providing clearance sufficient for the holder for the intervertebral disc prosthesis to position the intervertebral disc prosthesis into the guide.

18. Method for implanting of claim 7 in which the step of positioning the guide is performed with a holder for the guide configured to engage at least two notches of the guide to provide clearance for tools for accessing the intervertebral space.

19. Method for implanting of claim 7 further comprising, before inserting the intervertebral disc prosthesis into the intervertebral space, the step of preparing the intervertebral space using a chisel having at least one blade, an adjustable stop and suitable shape and dimension for engagement with the guide and for cutting at least one notch in at least one vertebra.

20. Method for implanting of claim 19 further comprising the step of clearing the intervertebral space of the bone debris generated by cutting the notch.

* * * * *